United States Patent
Kameyama et al.

(10) Patent No.: US 10,597,427 B2
(45) Date of Patent: Mar. 24, 2020

(54) DIABETES-INDUCIBLE BACTERIUM

(71) Applicant: AJINOMOTO CO., INC., Tokyo (JP)

(72) Inventors: Keishi Kameyama, Kawasaki (JP); Kikuji Itoh, Tokyo (JP)

(73) Assignee: AJINOMOTO CO., INC., Tokyo (JP)

( * ) Notice: Subject to any disclaimer, the term of this patent is extended or adjusted under 35 U.S.C. 154(b) by 848 days.

(21) Appl. No.: 14/498,410

(22) Filed: Sep. 26, 2014

(65) Prior Publication Data

US 2015/0079209 A1 Mar. 19, 2015

Related U.S. Application Data

(63) Continuation of application No. PCT/JP2013/057287, filed on Mar. 14, 2013.

(60) Provisional application No. 61/618,052, filed on Mar. 30, 2012.

(30) Foreign Application Priority Data

Mar. 30, 2012 (JP) ................ 2012-080469

(51) Int. Cl.
| | | |
|---|---|---|
| A61K 8/96 | (2006.01) | |
| C07K 14/195 | (2006.01) | |
| C12Q 1/689 | (2018.01) | |
| C12R 1/01 | (2006.01) | |
| A61K 39/08 | (2006.01) | |
| A61K 38/00 | (2006.01) | |

(52) U.S. Cl.
CPC .......... C07K 14/195 (2013.01); C12Q 1/689 (2013.01); C12R 1/01 (2013.01); *A61K 38/00* (2013.01); *A61K 39/08* (2013.01); *C07K 2317/76* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2006/0062774 | A1* | 3/2006 | Davis ............... | A61K 8/99 424/93.45 |
| 2006/0148045 | A1* | 7/2006 | Uchiyama ......... | A23C 9/123 435/125 |
| 2008/0193373 | A1* | 8/2008 | Stritzker ........... | A61K 33/24 424/1.17 |
| 2011/0206654 | A1* | 8/2011 | Hodin .............. | A61K 31/43 424/94.6 |
| 2011/0280840 | A1 | 11/2011 | Blaser et al. | |

FOREIGN PATENT DOCUMENTS

| | | | |
|---|---|---|---|
| WO | WO 2010/092164 | A2 | 8/2010 |
| WO | WO 2012/024638 | A2 | 2/2012 |

OTHER PUBLICATIONS

Eggerth et al. J. Bacteriol. Apr. 1933 vol. 25 No. 4 389-413.*
Bärbel Stecher, et al., "*Salmonella enterica* Serovar Typhimurium Exploits Inflammation to Compete with the Intestinal Microbiota" Inflammation Impairs Colonization Resistance, PLoS Biology; vol. 5, No. 10, Oct. 2007, pp. 2177-2189.
Stecher B. et aL., "Uncultured bacterium clone 16saw23-2g06.plk 16S ribosomal RNA gene", partial sequence, Database DDBJ/EMBL/GeneBank, Accession No. EF605067, Uncultured Bacterium, GenBank:EF605067.1, XP003033890, 2007, 1 page.
Wen L., et al., Uncultured bacterium clone H79S1_71b0716S ribosomal RNA gene, partial sequence, Database DDBJ/EMBL/GeneBank, Accession No. EU453312, Uncultured Bacterium, GeneBank: EU453312, 2008, 1 page.
Wen L., et al., "Innate immunity and intestinal microbiota in the development of Type1 diabetes." Nature, 2008, 23, vol. 455, nature07336, 6 pages.
S. Brugman et al., "Antibiotic treatment partially protects against type 1 diabetes in the Bio-Breeding diabetes-prone rat. Is the gut flora involved in the development of type 1 diabetes?", Diabetologia 2006, 49, pp. 2105-2108.
Ricardo Valladares, et al., "Lactobacillus Johnsonii N6.2 Mitigates the Development of Type 1 Diabetes in BB-DP Rats", PLoS one, May 2010, vol. 5, Issue 5, e10507, 9 pages.
Patrice D. Cani, et al., "The gut microbiome as therapeutic target", Pharmacology & Therapeutics, 130, 2011, pp. 202-212.
Patrice D. Cani, et al., "Changes in Gut Microbiota Control Metabolic Endotoxemia-Induced Inflammation in High-Fat Diet-Induced Obesity and Diabetes in Mice", Diabeteres 2008, vol. 57, Jun. 2008, pp. 1470-1481.
Mathieu Membrez, et al., "Gut microbiota modulation with norfloxacin and ampicillin enhances glucose tolerance in mice", The FASEB Journal, Research Communication, Jul. 2008, vol. 22, pp. 2416-2426.
Patrice D. Cani, et al., "Selective increases of bifidobacteria in gut microflora improve high-fat-diet-induced diabetes in mice through a mechanism associated with endotoxaemia", Diabetologia, 2007, 50, pp. 2374-2383.
P D Cani, et al., "Changes in gut microbiota control inflammation in obese mice through a mechanism involving GLP-2-driven improvement of gut permeability", Inflammatory Bowel Disease, Gut 2009, 58, 14 pages.
Extended Search Report dated Sep. 25, 2015 in European Patent Application No. 13769593.8.
Kristina Harris, et al., "Is the gut microbiota a new factor contributing to obesity and its metabolic disorders?", Journal of Obesity, vol. 53, No. 3, 2012, Article ID879151, XP055070564,15 pages.
Keishi Kameyama, et al., "Intestinal colonization by a Lachnospiraceae bacterium contributes to the development of diabetes in obese mice", Microbes and Environments, vol. 29, No. 4, 2014, XP055213151, pp. 427-430.
C. Bleuven et al., Proc. R. Soc. B, vol. 283: 20161458 (2016).

* cited by examiner

*Primary Examiner* — Julie Wu
*Assistant Examiner* — Douglas F White
(74) *Attorney, Agent, or Firm* — Oblon, McClelland, Maier & Neustadt, L.L.P.

(57) ABSTRACT

The present invention provides a diabetes-inducing bacterium and use thereof, and a reagent and a detection method for detecting the bacterium. According to the present invention, enteric colonization of the diabetes-inducing bacterium can be prevented, and diabetes can be treated and/or prevented.

6 Claims, 10 Drawing Sheets

Specification includes a Sequence Listing.

(before vancomycin administration)

(4 weeks after vancomycin treatment)

DIABETES-INDUCIBLE BACTERIUM

CROSS REFERENCES TO RELATED APPLICATIONS

This application is a continuation of International Patent Application No. PCT/JP2013/057287, filed on Mar. 14, 2013, and claims priority to Japanese Patent Application No. 2012-080469, filed on Mar. 30, 2012, and US Provisional Patent Application No. 61/618,052, filed on Mar. 30, 2012, all of which are incorporated herein by reference in their entireties.

BACKGROUND OF THE INVENTION

Field of the Invention

The present invention relates to a bacterium that induces the onset of diabetes and use thereof, as well as a detection method of the above bacterium and the like.

Discussion of the Background

Diabetes is a refractory disease that causes various complications since metabolic disorders including chronic hyperglycemia persist as a main pathology. Diabetes is classified based on the causal factor into type 1 diabetes, type 2 diabetes, diabetes due to genetic abnormality, diabetes associated with other disease or conditions, gestational diabetes and the like. Type 1 diabetes and type 2 diabetes are multi-factor disease developed by single nucleotide polymorphism (SNP), which is one of the genetic polymorphism rather than gene abnormality, added with various environmental factors. Type 1 diabetes is a diabetes developed when plural SNPs involved in autoimmunity and destruction of pancreatic β cells are added with environmental factors such as viral infection and the like to cause insulin deficiency resulting from the destructive lesion of pancreatic β cells (non-patent document 1). Type 2 diabetes is a diabetes developed when SNPs involved in insufficient insulin actions such as insulin secretion, insulin sensitivity and the like and SNPs involved in obesity are added with environmental factors such as overeating, high-fat diet, aging, smoking, lack of exercise and the like to cause abnormal signal transduction of insulin in adipose tissue, skeletal muscle and liver. Among the causal factors of type 2 diabetes, lowering of insulin sensitivity is dominant in Europeans and Americans, and lowering of insulin secretion capability of the pancreas also accompanies frequently in Japanese people (non-patent document 2).

While what causes the onset of diabetes is not completely clear, it is generally considered that type 2 diabetes is developed when people genetically prone to diabetes (genetic factor) acquire a lifestyle easily leading to diabetes (environmental factor).

As one of the environmental factors involved in the onset of diabetes, involvement of enteric bacteria has been clarified in recent years. In type 1 diabetes, it has been reported that the onset of diabetes in type 1 diabetes model rat was suppressed by drinking-water ingestion of a mixed aqueous solution of antibiotics including sulphamethoxazole, trimethoprime and colistine (non-patent document 3), and the symptoms of diabetes in type 1 diabetes model rat were mitigated by the administration of probiotics lactic acid bacterium *Lactobacillus johnsonii* N6.2 (non-patent document 4). There are more number of reports on the involvement of enteric bacteria in the onset of type 2 diabetes. Since increased insulin and inflammatory cytokine due to obesity act on the tight junction of the intestinal epithelial cells to increase paracellular permeability, and therefore, lipopolysaccharide (LPS), which is an enteric gram negative bacteria-derived cellular constituent component, can easily invade into the living organism. LPS taken into the portal vein is delivered to the liver, and recognized by Kupffer cell, which is a mononuclear cell in the liver, which triggers the release of inflammatory cytokine. As a result, insulin resistance of the liver is induced, and abnormal sugar metabolism and lipid metabolism are developed. Therefore, gluconeogenesis and glycogenolysis in the liver, which are intrinsically to be suppressed by insulin, are promoted to develop hyperglycemia. Also, LPS that invaded into the blood is similarly recognized by mononuclear cells such as macrophage and the like, which induces secretion of inflammatory cytokine, and decreases insulin sensitivity of skeletal muscles and adipose tissues. As a result, sugar uptake is suppressed and hyperglycemia is developed (reported in non-patent document 5).

In 2008, Cani et al. reported that administration of ampicillin and neomycin in drinking water to high-fat diet ingested mouse improves fasting blood glucose level, glucose tolerance, insulin resistance, and inflammation in adipose tissue (non-patent document 6). Furthermore, Membrez et al. reported in 2008 that administration of norfloxacin and ampicilin in drinking water to ob/ob mouse and high-fat diet ingested mouse significantly improves the fasting blood glucose level and glucose tolerance (non-patent document 7).

As for the type 2 diabetes improving effect of prebiotics, moreover, Cani et al. reported in 2007 and 2009 that the pathology of type 2 diabetes is improved by an increase in enteric bifidobacteria due to oligosaccharide (non-patent documents 8, 9).

DOCUMENT LIST

Non-Patent Documents non-patent document 1: Insulin Secretion, Bunkodo, 2004, pages 43-52
non-patent document 2: Insulin Resistance, Bunkodo, 2004, pages 35-44
non-patent document 3: Diabetologia 2006, 49, 2105-2108
non-patent document 4: PLoS One 2010, 5, e10507
non-patent document 5: Pharmacol Ther 2011, 130, 202-212
non-patent document 6: Diabetes 2008, 57, 1470-1481
non-patent document 7: FASEB J 2008, 22, 2416-26
non-patent document 8: Diabetologia 2007, 50, 2374-83
non-patent document 9: Gut 2009, 58, 1091-1103

SUMMARY OF THE INVENTION

Problems to be Solved by the Invention

As mentioned above, the deep involvement of enteric bacterial flora has been suggested as one of the environmental factors relating to the development of the pathology of type 1/type 2 diabetes. However, since all reports relate to the use of antibiotics having a broad antibacterial spectrum or the use of prebiotics, they merely clarified the involvement of enteric bacterial flora as a whole with a complex system, and have not found the involvement limited to a particular enteric bacterium. There is no earlier report on a particular enteric bacterium that causes pathology development of diabetes, and whether or not such enteric bacterium is present is also completely unknown.

While the treatment effect of antibiotic on diabetes is sufficiently expected, the use of an antibiotic having a broad antibacterial spectrum poses problems since it simultaneously removes useful enteric bacteria such as bifidobacteria, lactic acid bacterium and the like, increases the risk of emergence of antibiotic resistant bacteria, markedly decreases the QOL of patients due to the side effect diarrhea and the like.

Therefore, if the bacterium that causes pathology expression of diabetes can be identified, diabetes can be effectively treated or prevented by developing a removal method that specifically acts on the bacterium. In view of the above situation, an object the present invention is to isolate and identify a bacterium that induces diabetes, and provide a means for the treatment and/or prophylaxis of diabetes by utilizing the bacterium.

Means of Solving the Problems

The present inventors have conducted intensive studies in an attempt to solve the aforementioned problems, comprehensively examined the enteric bacterial flora in the feces of obesity model mice that showed a high fasting blood glucose level exceeding 400 mg/dl, compared the value with that of normal mice, and found that a particular bacterium has become dominant. They have succeeded in isolating this bacterium from the contents of the cecum of the obesity model mice. They have further performed a phylogenetic system analysis based on the 16S ribosomal RNA gene sequence thereof and, as a result, found that it is a new species of a new genus belonging to Lachnospiraceae. They have further clarified that the bacterium causes lowering of insulin secretion capability and hyperglycemia when it is colonized in the intestine of germ-free obesity model mice. The present invention has been completed based on the above findings.

Accordingly, the present invention is as described below.
[1] A bacterium having a diabetes inducing activity, which belongs to Lachnospiraceae.
[2] The bacterium of [1], which is *bacillus*.
[3] The bacterium of [1] or [2], which has a pilus or flagellum-like structure.
[4] The bacterium of any of [1]-[3], which has motility.
[5] The bacterium of any of [1]-[4], which is anaerobic.
[6] The bacterium of any of [1]-[5], which shows ethanol resistance.
[7] The bacterium of any of [1]-[6], which is an enteric bacterium.
[8] A bacterium having a 16S ribosomal RNA gene comprising a nucleic acid sequence having a homology of not less than 98% to the nucleic acid sequence shown by SEQ ID NO: 3.
[9] A bacterium having a 16S ribosomal RNA gene comprising the nucleic acid sequence shown by SEQ ID NO: 3.
[10] The bacterium of [8] or [9], having an activity to induce diabetes.
[11] The bacterium of any of [1]-[10], which is identified by the accession number FERM BP-11443.
[12] A reagent for detecting the bacterium of any of [1]-[11], which comprises a primer set or probe that specifically detects a 16S ribosomal RNA gene comprising a nucleic acid sequence having a homology of not less than 98% to the nucleic acid sequence shown by SEQ ID NO: 3.
[13] The reagent of [12], which comprises a primer set or probe that specifically detects a 16S ribosomal RNA gene comprising the nucleic acid sequence shown by SEQ ID NO: 3.
[14] The reagent of [12] or [13], wherein the primer set comprises a polynucleotide that hybridizes to a continuous partial sequence of a complementary sequence of a nucleic acid sequence shown by any of SEQ ID NOs: 4-12 and a polynucleotide that hybridizes to a continuous partial sequence of a nucleic acid sequence shown by any of SEQ ID NOs: 4-12, which is on the 3' side from said hybridization site.
[15] The detection reagent of any of [12]-[14], wherein the primer set comprises a polynucleotide consisting of the nucleic acid sequence shown by SEQ ID NO: 1 and a polynucleotide consisting of the nucleic acid sequence shown by SEQ ID NO: 2.
[16] The detection reagent of [12] or [13], wherein the probe comprises a polynucleotide that hybridizes to a continuous partial sequence of a nucleic acid sequence shown by any of SEQ ID NOs: 4-12 or a complementary sequence thereof.
[17] The detection reagent of any of [12], [13] and [16], wherein the probe comprises a polynucleotide consisting of the nucleic acid sequence shown by SEQ ID NO: 1 or a polynucleotide consisting of the nucleic acid sequence shown by SEQ ID NO: 2.
[18] A method of detecting the bacterium of any of [1]-[11], comprising specifically detecting 16S ribosomal RNA gene comprising a nucleic acid sequence having a homology of not less than 98% to the nucleic acid sequence shown by SEQ ID NO: 3.
[19] The detection method of [18], comprising specifically detecting 16S ribosomal RNA gene comprising the nucleic acid sequence shown by SEQ ID NO: 3.
[20] The detection method of [18] or [19], comprising performing a polymerase chain reaction using, as a primer, a polynucleotide that hybridizes to a continuous partial sequence of a complementary sequence of a nucleic acid sequence shown by any of SEQ ID NOs: 4-12, and a polynucleotide that hybridizes to a continuous partial sequence of a nucleic acid sequence shown by any of SEQ ID NOs: 4-12, which is on the 3' side from said hybridization site.
[21] The detection method of [20], comprising performing a polymerase chain reaction using, as a primer, a polynucleotide consisting of the nucleic acid sequence shown by SEQ ID NO: 1 and a polynucleotide consisting of the nucleic acid sequence shown by SEQ ID NO: 2.
[22] The detection method of [18] or [19], comprising using, as a probe, a polynucleotide that hybridizes to a continuous partial sequence of a nucleic acid sequence shown by any of SEQ ID NOs: 4-12 or a complementary sequence thereof.
[23] The detection method of [22], comprising using, as a probe, a polynucleotide consisting of the nucleic acid sequence shown by SEQ ID NO: 1 or a polynucleotide consisting of the nucleic acid sequence shown by SEQ ID NO: 2.
[24] The detection method of [18] or [19], comprising detecting a restriction enzyme-treated fragment having a fragment length of 282±1 bp by a T-RFLP method using restriction enzyme MspI.
[25] A method of judging the presence or absence of a predisposing cause of diabetes, comprising detecting the bacterium of any of [1]-[11] in the feces of a test subject.
[26] The judgment method of [25], wherein the bacterium is detected by the detection method of any of [18]-[24].
[27] An agent for judging the presence or absence of the predisposing cause of diabetes, comprising a primer set or probe that specifically detects a 16S ribosomal RNA gene comprising a nucleic acid sequence having a homology of not less than 98% to the nucleic acid sequence shown by SEQ ID NO: 3.

[28] The agent of [27], comprising a primer set or probe that specifically detects 16S ribosomal RNA gene comprising the nucleic acid sequence shown by SEQ ID NO: 3.

[29] The agent of [27] or [28], wherein the primer set comprises a polynucleotide that hybridizes to a continuous partial sequence of a complementary sequence of a nucleic acid sequence shown by any of SEQ ID NOs: 4-12 and a polynucleotide that hybridizes to a continuous partial sequence of a nucleic acid sequence shown by any of SEQ ID NOs: 4-12, which is on the 3' side from said hybridization site.

[30] The agent of any of [27]-[29], wherein the primer set comprises a polynucleotide consisting of the nucleic acid sequence shown by SEQ ID NO: 1 and a polynucleotide consisting of the nucleic acid sequence shown by SEQ ID NO: 2.

[31] The agent of [27] or [28], wherein the probe comprises a polynucleotide that hybridizes to a continuous partial sequence of a nucleic acid sequence shown by any of SEQ ID NOs: 4-12 or a complementary sequence thereof.

[32] The agent of any of [27], [28] and [31], wherein the probe comprises a polynucleotide consisting of the nucleic acid sequence shown by SEQ ID NO: 1 or a polynucleotide consisting of the nucleic acid sequence shown by SEQ ID NO: 2.

[33] A processed product of the bacterium of any of [1]-[11].

[34] The processed product of [33], which is one or more selected from a dead cell, a constituent component and an extract of the bacterium of any of [1]-[11].

[35] A composition for inducing an immune response to the bacterium of any of [1]-[11], which comprises the processed product of [33] or [34].

[36] The composition of [35], which is for the treatment and/or prophylaxis of diabetes.

[37] A polynucleotide comprising the nucleic acid sequence shown by SEQ ID NO: 3.

[38] An antibody that specifically recognizes the bacterium of any of [1]-[11] or an antigenic constituent component, which is contained in the bacterium.

[39] A method for the treatment and/or prophylaxis of diabetes induced by the bacterium of [1], comprising administering a composition comprising a processed product of the bacterium of [1] to a subject.

Effect of the Invention

The bacterium of the present invention has an activity to induce diabetes. Therefore, suppression of the colonization, growth or physiological action of the bacterium of the present invention can be a new strategy not only for the treatment of diabetes but also for the prophylaxis thereof. Conventionally, insulin preparation, insulin secretagogue, insulin sensitizer, glucose absorption inhibitor and the like are well known as therapeutic drugs for diabetes; however, all of them are medicaments for symptomatic therapy. The present invention enables removal of enteric bacterium causing diabetes. This is a causative therapeutic method for treating diabetes, which has never been found heretofore. A vaccine composition of the present invention, which specifically acts on the enteric bacterium, enables prevention of colonization of the enteric bacterium before the onset of diabetes, and becomes a new means for reducing the risk of diabetes from the aspect of preventive medicine.

DETAILED DESCRIPTION OF THE PREFERRED EMBODIMENTS

Figure 1:
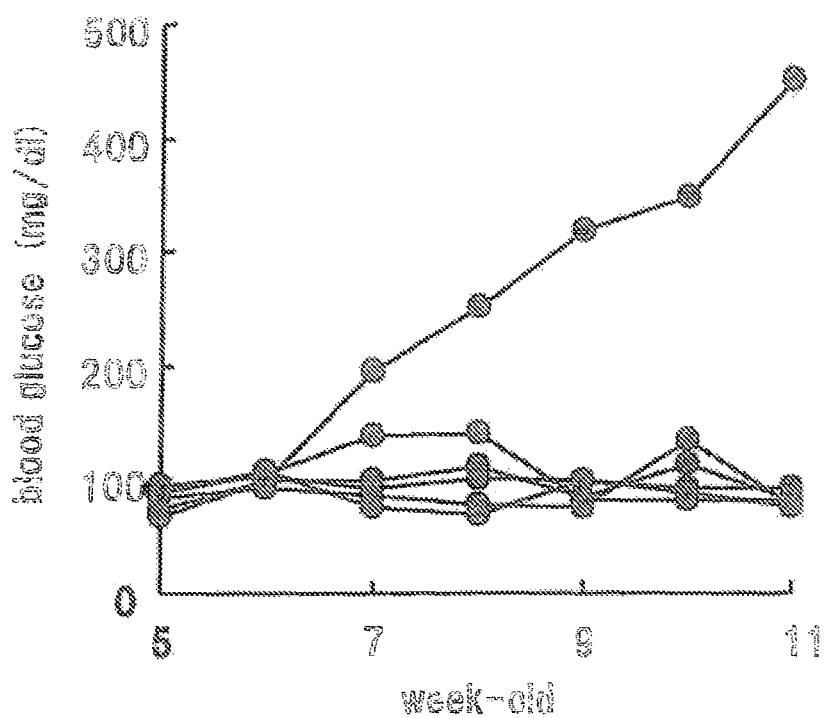
FIG. 1 shows a time course changes of the fasting blood glucose level of ob/ob mice.

1. Bacterium Having an Activity to Induce Diabetes

The present invention relates to an enteric bacterium having an activity to induce diabetes. The diabetes includes both type 1 diabetes and type 2 diabetes.

The activity to induce diabetes can be judged based on the presence or absence of either of the activities to induce insulin resistance and induce lowering of insulin secretion capability. The activity to induce insulin resistance and the activity to induce lowering of insulin secretion capability can be judged by any method, which is not particularly limited as long as such activities can be judged and, for example, can be judged by the following method.

In a method for judging the activity to induce lowering of insulin secretion capability, 5-week-old germ-free male C57BL/6JHamSlc-ob/ob mice are acclimated until 8-week-old under germ-free conditions. During the entire period up to the completion of breeding, the mice are bred in an isolator capable of maintaining the germ-free conditions, and allowed to freely take water and a general feed (e.g., CRF-1 (manufactured by Oriental Yeast Co., Ltd.)). Thereafter, they are divided into a control (germ-free) group, and an *E. coli* and test enteric bacterium co-colonization group (co-colonization group). The co-colonization group is orally inoculated with cultivated bacteria of *E. coli* (about $10^7$ cells) and cultivated bacteria of test enteric bacterium (about $10^7$ cells) for gnotobiotication. The control group is administered only with a medium used for a suspension of bacteria.

After breeding the mice of each group for 6 more weeks, they were fasted for 4 hr, and the blood glucose level, blood insulin concentration, blood glucagon concentration are measured. When the blood glucose level and the blood glucagon concentration of the co-colonization group are statistically significantly high as compared to those of the control group, and an average blood insulin concentration of the co-colonization group is statistically significantly low as compared to that of the control group, the test enteric bacterium can be judged to have an activity to induce diabetes.

In a method for judging the activity to induce insulin resistance, C57BL/6J mice (Charles River Laboratories Japan) induced to have obesity with a high-fat diet with 60 kcal % lard (manufactured by Research Diet) from 4-week-old to 12-week-old are used. The mice are divided into two groups of a control group and a test enteric bacterium administration group. The test enteric bacterium administration group is loaded with a test enteric bacterium (prepared when in use at a dose of about $10^6$ cells/350 μl/mouse) once per day for 4 weeks by oral administration. The control group is administered only with a medium used for a suspension of bacteria. The mice were bred under SPF conditions and allowed to freely take water and a high-fat diet with 60 kcal % lard.

At 4 weeks from the start of the bacteria administration, an insulin tolerance test (insulin 1 U/kg, i.p.) is performed to examine an influence on the insulin resistance. When a decrease in the blood glucose level of the test enteric bacterium administration group 15 min-45 min after the insulin administration is statistically significantly suppressed as compared to the control group, the test enteric bacterium can be judged to have an activity to induce diabetes.

The bacterium of the present invention is judged to have an activity to induce diabetes by at least one, preferably both, of the above-mentioned method for judging the insulin resistance inducing activity and the method for judging the activity to induce lowering of insulin secretion capability.

The bacterium of the present invention belongs to Phylum: Firmicutes Clostridia Clostridiales Lachnospiraceae. Whether the bacterium isolated from a separation source belongs to Lachnospiraceae can be determined by, for example, comparing the base sequence data of 16S ribosomal RNA gene and the sequence data of a known species and performing a lineage analysis. The steps for the lineage analysis and a method of forming a phylogenic tree are, for example, as follows.

First, a genomic DNA to be the template is extracted from a bacterium. A method of extracting a DNA from a bacterium is known, and any method can be used. In general, a method including treating a bacterium with a bacterial wall degrading enzyme such as lysozyme and the like, a physical destruction method using glass beads, a treatment method including repeating freeze-thawing and the like are used. Commercially available DNA extraction reagents can also be used. The genomic DNA does not always need to be extracted in an intact state. Therefore, a method having a low possibility of sample contamination, which is easily and rapidly operated, can be appropriately selected.

Then, a target DNA encoding 16S ribosomal RNA is amplified by a polymerase chain reaction (PCR). The primer sequence used for PCR can be appropriately designed so that a target DNA encoding 16S ribosomal RNA of at least all of the known bacteria belonging to Lachnospiraceae will be amplified. Generally, a primer consisting of a sequence preserved beyond the biological species (universal primer) is used. The PCR conditions are not particularly limited, and can be appropriately selected within the range generally used. The reaction can be performed using a commercially available PCR reagent and according to the attached instruction sheet.

The DNA fragment amplified by PCR is purified by using a spin column and the like as necessary, and the base sequence thereof is determined. The base sequence can be determined according to a conventional method.

Using a suitable gene sequence database and homology search program, a homology search is performed between the determined sequence and known bacterial 16S ribosomal DNA sequences, a known sequence with the highest homology can be extracted. For example, FASTA and BLAST can be utilized through the website of the DNA Data Bank of Japan (DDBJ). When a search is performed by selecting blastn and fasta as a program, using the determined nucleotide sequence as a query, and selecting 16S rRNA (Prokaryotes) as the search target database, a known sequence showing high homology is extracted and output. As long as the data set of the base sequence of 16S ribosomal RNA gene of the bacteria is contained, any other gene sequence database can also be used. In addition, a homology search program known per se, which is other than the above, can also be used.

As a result of the homology search, when the sequence of the 16S ribosomal RNA gene of the isolated bacteria shows a higher homology to a known sequence of a bacterium belonging to Lachnospiraceae than a known sequence of a bacterium not belonging to Lachnospiraceae, the bacterium can be identified as a bacterium belonging to Lachnospiraceae.

Alternatively, it is also possible to assume a molecular phylogenetic tree based on the nucleotide sequence of the amplified DNA, and identify the taxonomic position of the isolated bacteria. Molecular phylogenetic analysis software is published on the internet and the like, and can be utilized (CLUSTAL W, etc.). As a result of phylogenetic analysis, when the isolated bacterium is in the same cluster as that of the bacteria belonging to Lachnospiraceae, it can be identified as a bacterium belonging to Lachnospiraceae.

While the bacterium of the present invention may be obtained by any method, it can be isolated by a method of collecting from the feces of mammals suffering from diabetes, a method of directly collecting from the intestine of the mammal, a method of collecting from mouth, vagina, skin and the like. Since the bacterium of the present invention tends to be dominant in the intestinal bacterial flora of mammals suffering from diabetes, it can be easily isolated from the feces, the contents of the intestine and the like of the mammal. Therefore, the bacterium of the present invention is preferably an enteric bacterium.

Culture of the bacterium of the present invention can be carried out by a method known per se, which is generally used in the field. Whether or not the isolated bacteria have an activity to induce diabetes and/or belong to Lachnospiraceae can be further confirmed.

The bacterium of the present invention is generally a long *bacillus* of about 10 μm in length, about 1 μm in width under normal culture conditions (e.g., 37° C., anaerobic and the like). The bacterium of the present invention has a many pili or flagellum-like structure and has motility. The motility here means an ability to grow and spread throughout the culture medium from where it was inoculated, without forming colonies, and is an ability to move for the movement of the cells. The locomotion of the cells includes, but is not limited to, migrating motility, sliding motility, amoebic motility, surface motility, protoplasm motility and the like. To evaluate the motility, direct observation under a microscope, observation by agar plate culture, observation with semisolid stab culture medium and the like, and any of these can be used.

The bacterium of the present invention is anaerobic. The bacterium of the present invention can be cultured under anaerobic conditions (oxygen concentration 1 ppm or less) in a medium for enteric bacterial culture such as EG agar medium and the like.

Furthermore, when the bacterium of the present invention is present in the feces or cecum and intestinal contents, it shows resistance to an organic solvent (preferably ethanol), and characteristically loses resistance by pure culture. Therefore, the bacterium of the present invention is organic solvent resistant (preferably ethanol resistant). The organic solvent resistance (preferably ethanol resistance) here means that the feces or cecum and intestinal contents containing the bacterium, which were soaked for 2 hr in an organic solvent such as ethanol, chloroform and the like (preferably ethanol), has an ability to grow again in a suitable medium, regardless of the presence or absence of spore formation. The AJ110941 of the present invention is a bacterium isolated and cultured from the cecum contents of mice, which were suspended in chloroform or ethanol and allowed to stand for 2 hr. When the bacterium is present in the mice intestine, it is not killed by these organic solvents. However, bacteria that experienced pure culture once do not grow even when cultured under the same conditions after being processed with these organic solvents.

In one embodiment, the bacterium of the present invention comprises a 16S ribosomal RNA gene comprising a nucleic acid sequence having a homology of not less than 98% to the nucleic acid sequence shown by SEQ ID NO: 3, preferably a 16S ribosomal RNA gene comprising the nucleic acid sequence shown by SEQ ID NO: 3. SEQ ID NO: 3 shows the sequence of 16S ribosomal RNA gene of one (AJ110941 strain) of the bacteria of the present invention belonging to Lachnospiraceae to be described later. The homology between nucleic acid sequences is calculated using the above-mentioned homology search program BLAST. In general, for bacteria, not less than 95% of homology of 16S ribosomal RNA gene sequence is required for identification at the species level, and not less than 98% of 16S ribosomal RNA gene sequence for identification at the genus level (Science 2005, 307, 1915-1920). When the bacteria belong to the same species as the AJ110941 strain, the bacteria can be said to have a high possibility of having an activity to induce diabetes, like the AJ110941 strain.

The presence of the above-mentioned 16S ribosomal RNA gene in the bacterium can be confirmed by using the aforementioned analysis method of the base sequence of 16S ribosomal RNA gene. Alternatively, it can be examined by a method known per se (PCR, Southern blotting, DNA array etc.) by using a primer or probe capable of specifically detecting the gene, according to the reagent for detection and detection method of the present invention to be explained in detail below.

One embodiment strain (AJ110941) of the bacterium of the present invention isolated by the present inventors was internationally deposited under accession No. FERM BP-11443 in the National Institute of Advanced Industrial Science and Technology, the International Patent Organism Depositary (Central 6, 1-1-1 Higashi, Tsukuba, Ibaraki) under the Budapest Treaty (date of deposit: Nov. 30, 2011). AJ110941 strain was isolated from the cecum contents of diabetes model mice (BKS.Cg-m+/+Lepr$^{db}$/J(db/db) mice).

For the separation of AJ110941 strain, EG liquid medium converted to anaerobic medium ("probiotics.prebiotics.biogenics", Japan Bifidobacteria Center, 2006) and EG agar medium were used, and the culture was performed anaerobically.

Since the bacterium of the present invention can be a target for the prophylaxis and/or treatment of diabetes, as one factor of diabetes, it is useful for screening for an agent for the prophylaxis and/or treatment of diabetes. It is also useful as a starting material for the production of the vaccine composition of the present invention to be mentioned below.

The present invention also provides a polynucleotide comprising the nucleic acid sequence shown by SEQ ID NO: 3. SEQ ID NO: 3 shows the sequence of 16S ribosomal RNA gene of one (AJ110941 strain) of the bacteria of the present invention belonging to Lachnospiraceae.

The polynucleotide may be DNA or RNA, or may be a DNA/RNA chimera. The polynucleotide may be double stranded or single stranded. When the polynucleotide is double stranded, it may be double stranded DNA, double stranded RNA or DNA:RNA hybrid.

The polynucleotide of the present invention can be directly amplified by PCR by using a suitable primer designed by utilizing the information of known sequences and sequence information described in the Sequence Listing in the present specification, and using the full-length DNA of the AJ110941 strain, which is the bacterium of the present invention, and the like as a template. Alternatively, it may be synthesized by a polynucleotide synthesizer based on the sequence information.

The polynucleotide of the present invention is preferably isolated or purified. The "isolation or purification" means that an operation to remove components other than the object component from the naturally present state has been performed. The purity of the isolated or purified polynucleotide of the present invention (weight ratio of the polynucleotide of the present invention relative to the total polynucleotide weight) is generally not less than 50%, preferably not less than 70%, more preferably not less than 90%, most preferably not less than 95% (for example, substantially 100%).

The polynucleotide of the present invention can be used as a positive control for the detection of the bacterium of the present invention and is useful.

2. Reagent for Detecting the Bacterium of the Present Invention

The present invention provides a reagent for detecting the above-mentioned bacterium of the present invention.

The detection reagent in the present invention detects the presence of the bacterium of the present invention in a sample by detecting the sequence of the 16S ribosomal RNA gene of the bacterium of the present invention. The detection reagent in the present invention contains a primer or probe capable of specifically detecting a 16S ribosomal RNA gene comprising a nucleic acid sequence having a homology of not less than 98% to the sequence shown by SEQ ID NO: 3, preferably a 16S ribosomal RNA gene comprising the nucleic acid sequence shown by SEQ ID NO: 3.

The above-mentioned primer may be any as long as it is designed to specifically amplify by PCR a part of or the whole region of the above-mentioned 16S ribosomal RNA gene. Here, "specifically" means that the primer PCR amplifies a part of or the whole region of a 16S ribosomal RNA gene comprising a nucleic acid sequence having a homology of not less than 98% to the nucleic acid sequence shown by SEQ ID NO: 3, preferably a part of or the whole region of a 16S ribosomal RNA gene comprising the nucleic acid sequence shown by SEQ ID NO: 3, but does not PCR amplify a 16S ribosomal RNA gene of a bacterium other than Lachnospiraceae.

Examples of the above-mentioned primer include a pair of polynucleotides, which is a combination of a polynucleotide comprising a nucleic acid sequence of about 15-about 50 bases, preferably about 18-about 30 bases, that hybridizes to a continuous partial sequence of a complementary sequence of a nucleic acid sequence having a homology of not less than 98% to the nucleic acid sequence shown by SEQ ID NO: 3 (preferably, the nucleic acid sequence shown by SEQ ID NO: 3), and a polynucleotide comprising a nucleic acid sequence of about 15-about 50 bases, preferably about 18-about 30 bases, that hybridizes to a continuous partial sequence of the above-mentioned nucleic acid sequence on the 3' side from the above-mentioned hybridization site, which amplifies a nucleic acid having a fragment length of about 50-about 1,000 bases, preferably about 50-about 500 bases.

The primer preferably contains a nucleic acid sequence having a homology of not less than 98% to the nucleic acid sequence shown by SEQ ID NO: 3 (preferably, the nucleic acid sequence shown by SEQ ID NO: 3) or a continuous 15-50 base (preferably 18-30 base) partial sequence of a complementary sequence thereof.

From the aspect of specificity, a preferable primer includes a combination of a polynucleotide that hybridizes to a continuous partial sequence of a complementary sequence of a nucleic acid sequence shown by any of SEQ ID NOs: 4-12, and, using SEQ ID NO: 3 as a reference, a polynucleotide that hybridizes to a continuous partial sequence of a nucleic acid sequence shown by any of SEQ ID NOs: 4-12, which is on the 3' side from said hybridization site. More preferred is a combination of a polynucleotide comprising continuous 15-50 base (preferably 18-30 base) partial sequence of a nucleic acid sequence shown by any of SEQ ID NOs: 4-12, and a polynucleotide comprising a 15-50 base (preferably 18-30 base) continuous partial sequence of a complementary sequence of a nucleic acid sequence shown by any of SEQ ID NOs: 4-12, which is on the 3' side from said hybridization site to the polynucleotide consisting of the nucleic acid sequence shown by SEQ ID NO: 3 in said polynucleotide.

Specific examples of the preferable primer include a combination of a polynucleotide consisting of the nucleic acid sequence shown by the following SEQ ID NO: 1 and a polynucleotide consisting of the nucleic acid sequence shown by the following SEQ ID NO: 2:

```
161-183F:
                                        (SEQ ID NO: 1)
5'-CGCACAGCTTCGCATGAAGTGGT-3'

438-458R:
                                        (SEQ ID NO: 2)
5'-ACCGTCTGGCGACCCAAAGGT-3'
```

The temperature, reaction time and cycle number in PCR can be appropriately determined according to the amount of template DNA to be used, the kind of primer and the like. The annealing temperature in PCR can be appropriately determined based on the GC content of the primer. For example, the reaction can be performed using genomic DNA of the bacterium as a template, a polynucleotide consisting of the nucleic acid sequence shown by SEQ ID NO: 1 and a polynucleotide consisting of the nucleic acid sequence shown by SEQ ID NO: 2 as primers, and under the conditions of 30 cycles of 94° C. 30 seconds, 60° C. seconds, 72° C. 30 seconds.

The above-mentioned probe is a polynucleotide that hybridizes to a continuous nucleic acid sequence of not less than about 15 bases, preferably about 18-about 500 bases, more preferably about 18-about 200 bases, further preferably about 18-about 50 bases, which is contained in a nucleic acid sequence having a homology of not less than 98% to the nucleic acid sequence shown by SEQ ID NO: 3 (preferably, the nucleic acid sequence shown by SEQ ID NO: 3), or a complementary sequence of the continuous sequence under stringent conditions.

Hybridization can be performed according to a method known per se or a method analogous thereto, for example, the method described in Molecular Cloning, 2nd edition (J. Sambrook et al., Cold Spring Harbor Lab. Press, 1989) and the like. Examples of the stringent conditions include a hybridization reaction in 6×SSC (sodium chloride/sodium citrate) at 45° C., washing once or more with 0.2×SSC/0.1% SDS at 65° C. and the like. Those of ordinary skill in the art can easily adjust to desired stringency by appropriately changing the salt concentration of hybridization solution, temperature of hybridization reaction, probe concentration, probe length, number of mismatches, time of hybridization reaction, salt concentration of washing, temperature of washing and the like.

Preferably, the probe is a polynucleotide that comprises a continuous nucleic acid sequence of not less than about 15 bases, preferably about 18-about 500 bases, more preferably about 18-about 200 bases, further preferably about 18-about 50 bases, which is contained in a nucleic acid sequence having a homology of not less than 98% to the nucleic acid sequence shown by SEQ ID NO: 3 (preferably, nucleic acid sequence shown by SEQ ID NO: 3), or a complementary sequence of the continuous sequence.

The length of the probe is generally not less than about bases, preferably about 18-about 500 bases, more preferably about 18-about 200 bases, further preferably about 18-about 50 bases.

From the aspect of specificity, a preferable probe is a polynucleotide that hybridizes to a nucleic acid sequence shown by any of SEQ ID NOs: 4-12 or a complementary sequence thereof. More preferred is a polynucleotide containing a partial sequence of continuous 15-50 bases of a nucleic acid sequence shown by any of SEQ ID NOs: 4-12 or a complementary sequence thereof.

Specific examples of the preferable probe include a polynucleotide consisting of the nucleic acid sequence shown by SEQ ID NO: 1 or SEQ ID NO: 2.

The primer or probe may contain an additional sequence (nucleic acid sequence not complementary to the detection target polynucleotide), as long as the specific detection is not impaired.

A polynucleotide to be used as the aforementioned primer or probe may be a deoxyribonucleic acid (DNA) or a ribonucleic acid (RNA). When it is a ribonucleic acid, the thymidine residue (T) in the nucleotide sequence is appropriately deemed to be replaced by the uridine residue (U). It may also be a DNA containing a uridine residue synthesized by changing T at any position to U. It may also be an RNA containing a thymidine residue similarly synthesized by changing U at any position to T. Also, the polynucleotide may contain a point mutation such as deletion, insertion, substitution and the like, or a modified nucleotide, as long as it does not degrade the hybridization specificity.

In addition, the primer or probe may be labeled with a suitable labeling agent, for example, radioisotope (e.g., $^{125}$I, $^{131}$I, $^{3}$H, $^{14}$C, $^{32}$P, $^{33}$P, $^{35}$S etc.), enzyme (e.g., β-galactosidase, β-glucosidase, alkaline phosphatase, peroxidase, malic acid dehydrogenase etc.), fluorescent substance (e.g., fluorescamine, fluorescein isothiocyanate etc.), luminescence substance (e.g., luminol, luminol derivative, luciferin, lucigenin etc.), biotin and the like.

A polynucleotide to be used as the aforementioned primer or probe can be chemically synthesized using, for example, a general purpose DNA synthesizer. Polynucleotide may also be synthesized by any other method well known in the Technical Field.

The detection reagent of the present invention may further contain, as other components, nucleic acid synthase (DNA polymerase, RNA polymerase, reverse transcriptase and the like), other enzymes, substrate for enzyme (dNTP, rNTP and the like) and the like. It may also contain a label detection substance, buffer and the like.

Using the detection reagent of the present invention, the presence or absence of a pathogenic bacterium of diabetes in a sample can be easily judged in a short time. Therefore, the reagent is useful for the diagnosis of a predisposing cause of diabetes.

3. Detection Method of the Bacterium of the Present Invention

The present invention further provides a detection method of the bacterium of the present invention, comprising detecting 16S ribosomal RNA gene comprising a nucleic acid sequence having a homology of not less than 98% to the nucleic acid sequence shown by SEQ ID NO: 3, preferably 16S ribosomal RNA gene comprising the nucleic acid sequence shown by SEQ ID NO: 3.

In the present specification, the "detection of the bacterium of the present invention" encompasses not only judging the presence or absence of the cell of the bacterium of the present invention but also quantifying the amount of presence thereof.

For the detection of the bacterium of the present invention, total DNA is recovered from a sample. Examples of the kind of the sample include, but are not limited to, feces or the intestinal contents of a test subject (healthy human, diabetes patients or individual suspected of being affected with diabetes), isolated/cultured bacterium and the like. A method of isolating/purifying DNA from a sample is known in the technical field, and it can be performed by, for example, extraction with phenol-chloroform, extraction using a commercially available DNA extraction reagent, purification by a commercially available column kit and the like.

The DNA recovered from a sample is dissolved in an appropriate buffer, for example, TE (10 mM Tris-HCl, 1 mM EDTA, pH 8.0) and the like, and subjected to the detection method of the present invention.

In one embodiment, the detection method of the present invention includes performing PCR by using a primer contained in the above-mentioned detection reagent of the present invention, and DNA recovered from the sample as a template. The obtained PCR product is separated by electrophoresis (e.g., agarose gel electrophoresis, polyacrylamide gel electrophoresis etc.). After electrophoresis, the gel is stained with a staining solution known per se such as ethidium bromide solution and the like, and the PCR product is detected using a transilluminator and the like. Then, using the presence or absence or the amount of a specific PCR product as an index, the presence or absence and the amount of presence of the bacterium of the present invention in a sample is judged.

PCR used for the detection method of the present invention may be a quantitative PCR. The quantitative PCR can be performed by a known method, and two analysis methods are known. The first one utilizes the characteristics in that a reaction product exponentially increases to a certain amount and thereafter reaches the plateau in PCR reaction, and analyzes the amount of the reaction product in exponentially increasing phase and calculates the initial template amount. The second one determines the PCR cycle number (Ct) at which the amount of a reaction product exceeds a predetermined value (threshold) by monitoring real-time the reaction product. All these analysis methods require PCR by changing DNA amount at a known concentration, analysis of the reaction product at each cycle number, and determination of the range of quantitative PCR cycle number from the kinetics thereof. The amount of the object gene present in an unknown sample is roughly estimated from the results. As a result, the bacterium of the present invention presence in a sample can be quantified and, when even one copy of the object gene is estimated to be contained in the test sample, the bacterium of the present invention can be judged to be present.

In one embodiment, the detection method of the present invention includes a step of contacting a probe contained in the above-mentioned detection reagent of the present invention with total DNA or total RNA in a sample. The conditions for the contact are appropriately determined so that the probe will hybridize to a 16S ribosomal RNA gene or a gene product thereof to form a nucleic acid complex. The complex is detected to indicate the presence of the bacterium of the present invention.

The detection method of the present invention utilizing a probe can be performed by various known hybridization techniques (e.g., fluorescence in situ hybridization (hereinafter to be abbreviated as FISH)) and the like). In the FISH method, a probe enters into the cytoplasm of the bacterium, and hybridizes to a complementary sequence in the 16S ribosomal RNA gene present therein under appropriate hybridization conditions. When the probe is labeled with radioisotope, fluorescent substance (e.g., fluorescein isothiocyanate (FITC), TAMRA, Cy3, Cy5 and the like), chemical luminescence substance and the like, a specific hybridization phenomenon can be monitored by a suitable method (e.g., autoradiography, fluorescence microscope, flow cytometry and the like). For example, when the probe is labeled with radioisotope, an assay is performed by a method such as autoradiography and the like, when the probe is labeled with a fluorescent substance, an assay is performed by a method such as fluorescence microscope and the like, when the probe is labeled with a chemical luminescence substance, an analysis using a photosensitive film and a digital analysis using a CCD camera can be performed. In this way, the bacterium of the present invention in a sample can be detected.

In one embodiment, the detection method of the present invention includes detection of a restriction enzyme-treated fragment having a fragment length of 282±1 bp by a T-RFLP (Terminus Restriction Fragment Length Polymorphism) method using a restriction enzyme MspI.

For example, the T-RFLP method can be performed as follows. Total DNA is extracted from microorganism community in a sample and PCR is performed using the sequences common to all bacteria on the ribosomal RNA gene 8-27F: 5'-AGAGTTTGATCCTGGCTCAG-3' (SEQ ID NO: 13) and 1510-1492R: 5'-GGTTACCTTGTTAC-GACTT-3' (SEQ ID NO: 14) as primers. By labeling primer 8-27F with a fluorescent substance such as 6-carboxyfluorescein (6-FAM) and the like, the terminal of the obtained PCR product is labeled. The PCR product is digested with restriction enzyme MspI, electrophoresed using a capillary electrophoresis apparatus such as DNA sequencer (3130xl Genetic Analyzer manufactured by Applied Biosystems) and the like, under the conditions of size standard GS1200LIZ, 3130POP-7 polymer, 36 cm Capillary Array (all manufactured by Applied Biosystems), and a fragment containing the fluorescence-labeled terminal is detected. Under these conditions, the nucleic acid sequence shown by SEQ ID NO: 3 results in a 282±1 bp fragment having a restriction enzyme-treated terminal (Calculated: 287 bp+GC). Therefore, the bacterium of the present invention having a 16S ribosomal RNA gene containing the nucleic acid sequence shown by SEQ ID NO: 3 can be detected using the detection of a fragment having a restriction enzyme-treated terminal and a fragment length of 282±1 bp as an index.

Using the detection method of the present invention, the presence or absence of a pathogenic bacterium of diabetes in a sample can be easily judged in a short time. Therefore, the method is useful for the diagnosis of a predisposing cause of diabetes.

4. Judgment Method of the Presence or Absence of Predisposing Cause of Diabetes As shown in the below-mentioned Examples, the bacterium of the present invention was detected in the feces of the test subjects with type 2 diabetes at high frequency (7 out of 31). While the bacterium of the present invention was detected also in the obesity test subjects who had not developed diabetes (one out of 32), it was not detected in the healthy test subjects (0 out of 31). In consideration of the fact that the bacterium of the present invention has an activity to induce diabetes, the presence of the bacterium of the present invention in the intestine of the test subjects shows that they are prone to develop diabetes irrespective of whether the test subjects have already developed diabetes (the predisposing cause of diabetes). Therefore, the presence or absence of the predisposing cause of diabetes can be judged by detecting the bacterium of the present invention in the feces of a test subject. Thus, the present invention provides a judgment method of the presence or absence of the predisposing cause of diabetes, comprising detecting the bacterium of the present invention in the feces of a test subject.

The bacterium of the present invention can be detected by the detection method described in the above-mentioned 3, by using the feces of a test subject as a sample. When the bacterium of the present invention is detected in the feces of a test subject, the test subject can be judged to have the predisposing cause of diabetes, and have a relatively high risk of developing diabetes. Conversely, when the bacterium of the present invention is not detected, the test subject can be judged to have a relative low risk of developing diabetes.

Moreover, the present invention provides an agent for judging the presence or absence of the predisposing cause of diabetes. The agent of the present invention is used to judge the presence or absence of the predisposing cause of diabetes by detecting the presence of the bacterium of the present invention in the feces of a test subject. Therefore, the agent of the present invention preferably contains the detection reagent described in the above-mentioned 2, more preferably contains a primer set of a polynucleotide consisting of the nucleic acid sequence shown by SEQ ID NO: 1 and a polynucleotide consisting of the nucleic acid sequence shown by the following SEQ ID NO: 2. Using the agent of the present invention, the presence or absence of the predisposing cause of diabetes can be easily judged by the aforementioned method.

5. Processed Product of the Bacterium of the Present Invention and Composition Containing the Processed Product The present invention further provides a processed product of the above-mentioned bacterium of the present invention.

A processed product of the bacterium of the present invention is obtained by a physical or chemical treatment of the above-mentioned bacterium of the present invention such that its proliferative ability is irreversibly lost, and is not particularly limited as long as it can induce acquired immunity against the bacterium of the present invention. A processed product of the bacterium of the present invention is preferably any one or more selected from a dead cell, a constituent component and an extract of the bacterium of the present invention.

A dead cell of a bacterium can be prepared by sterilization of a living cell by a physical and/or chemical treatment according to a conventional method. Examples of the physical treatment method include a heat treatment (autoclave treatment, low temperature sterilization, high temperature sterilization and the like), a dry treatment (drying by heating, freeze-dry and the like), a electromagnetic treatment (UV sterilization, gamma ray sterilization and the like), a grinding and disrupture treatment (glass bead treatment, French Press treatment, sonication and the like) and the like, or a combination of these and the like. Examples of the chemical treatment method include a chemical medication treatment (formaldehyde treatment, surfactant treatment, acid treatment, alkali treatment), an enzyme treatment (protease treatment, enzymatic saccharification and the like) and the like, or a combination of these. For example, when a heat treatment is performed, a dead cell can be prepared by treating a living cell of the bacterium of the present invention at a temperature of about 80 to 120° C. for several seconds to about 30 min.

The constituent component of the bacterium can be prepared by isolating a part of the constituent component from a living cell or dead cell according to a conventional method. The constituent component of the bacterium of the present invention is not particularly limited as long as it can induce acquired immunity against the bacterium of the present invention. Examples thereof include protoplast obtained by treating bacteria with a cell wall-dissolving enzyme to remove cell wall, soluble component of bacteria with cell wall-dissolving enzyme, each fraction obtained by fractionation of a ground or disrupted product of bacteria by a known method and the like, as well as protein, nucleic acid, carbohydrates, lipid and the like obtained by further purification of these. These treatments are techniques well known in the technical field. Also, a polypeptide, a polypeptide or a protein obtained by synthesizing the protein or a part thereof present in the cell body of the bacterium of the present invention by genetic engineering or a chemical method can also be used as the constituent component of the bacterium of the present invention.

As an extract of the bacterium of the present invention, an extract obtained from a living cell or dead cell by various known extraction methods can be mentioned. Examples of the extraction method include various solvent extractions, supercritical fluid extraction and the like.

As a result of the above-mentioned treatments, a processed product of the bacterium of the present invention may lose antigenicity, or fail to induce acquired immunity against the bacterium of the present invention. Therefore, it is preferable to examine the antigenicity and other properties after the treatment.

Since a processed product of the bacterium of the present invention when administered to a target induces an immune response to the bacterium of the present invention, it is useful as an antigen and the like for producing an antibody recognizing the bacterium of the present invention.

The present invention further provides a composition for inducing an immune response to the bacterium of the present invention, which contains the above-mentioned processed product of the bacterium of the present invention. Since the composition of the present invention contains a processed product of the bacterium of the present invention as an antigen, it can induce an immune response to the bacterium of the present invention. By administering an immune response-induction amount of a processed product of the bacterium of the present invention to a mammal, an immune response to the bacterium of the present invention can be induced in the mammal.

Examples of the mammal include rodents such as mouse, rat, hamster, guinea pig and the like, and experiment animals such as rabbit and the like, pets such as dog, cat and the like, domestic animals such as bovine, swine, goat, horse and sheep and the like, primates such as human, monkey, orangutan and chimpanzee and the like, and the like. The mammals are preferably rodents (mouse etc.) or primates (human etc.).

The composition of the present invention may contain any carrier, for example, a pharmaceutically acceptable carrier, according to the dosage form. Examples of the pharmaceutically acceptable carrier include, but are not limited thereto, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropyl starch, sodium-glycol-starch, sodium hydrogen carbonate, calcium phosphate, calcium citrate and the like, lubricants such as magnesium stearate, aerosil, talc, sodium lauryl sulfate and the like, buffers such as phosphate buffer, acetate buffer, borate buffer, carbonate buffer, citrate buffer, tris buffer, glutamic acid, epsilon aminocaproic acid and the like, isotonic agents such as sodium chloride, potassium chloride, glycerol, mannitol, sorbitol, boric acid, glucose, propylene glycol and the like, pH adjusters such as hydrochloric acid, sodium hydroxide, phosphoric acid, acetic acid and the like, solubilizers such as glycerol, propylene glycol, macrogol, polyoxyethylene hydrogenated castor oil and the like, water-soluble cellulose derivatives such as methylcellulose, hydroxyethylcellulose, hydroxypropylmethylcellulose, carboxymethylcellulose and the like, thickeners such as sodium chondroitin sulfate, sodium hyaluronate, carboxyvinyl polymer, polyvinyl alcohol, polyvinylpyrrolidone, macrogol and the like, aromatics such as citric acid, menthol, glycyllysin.ammonium salt, glycine, orange powder and the like, preservatives such as sodium benzoate, sodium bisulfite, methylparaben, propylparaben and the like, stabilizing agents such as citric acid, sodium citrate, acetic acid, sodium bisulfite, sodium thiosulfate, sodium edetate, ascorbic acid, dibutylhydroxytoluene and the like, preservatives such as benzoic acid, paraoxybenzoates, sodium dehydroacetate, benzyl alcohol, chlorobutanol, phenol, cresol, benzalkonium chloride, benzethonium chloride and the like, suspensions such as methylcellulose, polyvinylpyrrolidone, aluminum stearate and the like, dispersing agents such as surfactant and the like, diluents such as water, saline, orange juice and the like, base wax such as cacao butter, polyethylene glycol, white kerosene and the like, deactivators such as formalin and the like, and the like.

The composition of the present invention preferably further contains a pharmaceutically acceptable adjuvant compatible with the active ingredient. An adjuvant is generally a substance that non-specifically potentiates an immune response of a host, and a number of various adjuvants are known in the technical field. Examples of the adjuvant include, but are not limited to, the following: aluminum hydroxide, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycerol-3-hydroxyphosphoryloxy)-ethylamine (MTP-PE), Quill A (registered trade mark), lysolecithin, saponin derivative, pluronicpolyol, montanide ISA-50 (Seppic, Paris, France), Bayol (registered trade mark) and Markol (registered trade mark).

The composition of the present invention can be produced by a conventional method. A processed product of the bacterium of the present invention only needs to be contained in the composition of the present invention in a proportion of 0.001-99.999 wt %.

The composition of the present invention can be administered through various pathways. Examples of the administration route include, but are not limited to, intradermal, subcutaneous, sublingual, intranasal, intramuscular, intraperitoneal, and oral route and the like. Particularly, a method inducing the mucosal immunity of the intestine is effective, and it is desirably made to act on small intestinal peyer's patch by protection by inclusion in an enteric capsule or a chemical modification.

While the dose of the composition of the present invention is determined in consideration of use, age, sex, body weight of the target, drug tolerability and the like, 0.001 mg-1,000 mg of the composition can be generally administered once or more times. Preferred is plural administrations and, in this case, the composition is preferably administered in the intervals of 2-4 weeks.

The composition of the present invention potentiates a specific immune response to the bacterium of the present invention having an activity to induce diabetes, and therefore, can remove the bacterium of the present invention without removing other useful enteric bacteria from the intestine. Accordingly, the composition of the present invention is useful as a vaccine for the prophylaxis and/or treatment of diabetes induced by the bacterium of the present invention. In this case, the subject of administration of the composition of the present invention is a mammal (e.g., human) affected with or having a risk of being affected with diabetes induced by the bacterium of the present invention. For example, an immune response induction amount of the bacterium of the present invention is administered to a mammal (e.g., human) free of the bacterium of the present invention, whereby an immune response to the bacterium of the present invention is induced in the mammal and the immunity to the bacterium of the present invention is acquired. Even when the bacterium of the present invention invades into the body of the mammal having the acquired immunity to the bacterium of the present invention, the acquired immunity acts to immunologically remove the bacterium of the present invention. Therefore, the onset of diabetes caused by the bacterium of the present invention can be prevented. Alternatively, an immune response induction amount of the bacterium of the present invention is administered to a mammal (e.g., human) carrying the bacterium of the present invention but has not developed diabetes yet, whereby an immune response to the bacterium of the present invention is induced in the mammal and the immunity to the bacterium of the present invention is acquired. As a result, the bacterium of the present invention is immunologically removed and the onset of diabetes caused by the bacterium of the present invention can be prevented. Furthermore, an immune response induction amount of the bacterium of the present invention is administered to a mammal (e.g., human) carrying the bacterium of the present invention and has developed diabetes, whereby an immune response to the bacterium of the present invention is induced in the mammal and the immunity to the bacterium of the present invention is acquired. As a result, the bacterium of the present invention is immunologically removed and the diabetes caused by the bacterium of the present invention can be treated.

In addition, the composition of the present invention is also useful as an immunogen for producing an antibody (monoclonal antibody, polyclonal antibody etc.) against the bacterium of the present invention.

Furthermore, the present invention provides an antibody that specifically recognizes the bacterium of the present invention or a constituent component having antigenicity, which is contained in the bacterium (hereinafter to be also referred to as the antibody of the present invention). An antibody that specifically recognizes the bacterium of the present invention refers to an antibody that specifically recognizes and binds to a surface antigen present on the cell surface of the bacterium of the present invention. Examples of the surface antigen include polysaccharide, peptidoglycan or protein present on pilus or flagellum. In addition, an antibody that specifically recognizes an antigenic constituent component contained in the bacterium of the present invention refers to an antibody that specifically recognizes and binds to not only a surface antigen but also a constituent component of the bacterium of the present invention. The constituent component of the bacterium of the present invention is as described for the above-mentioned processed product of the bacterium of the present invention. For example, a protein encoded on the genome of the bacterium of the present invention (including intracellular protein and secretion protein) and the like are included.

The antibody of the present invention can be produced by an existing general production method and using a processed product of the above-mentioned bacterium of the present invention or the composition of the present invention as an immunogen. In the present specification, examples of the antibody include, but are not limited to, natural antibodies such as polyclonal antibody, monoclonal antibody (mAb) and the like, chimera antibody, humanized antibody, human antibody and single strand antibody produced by gene recombination technique, and binding fragments thereof. Preferably, the antibody is a polyclonal antibody, a monoclonal antibody or a binding m fragment thereof. The binding fragment means a partial region of the aforementioned antibody having a specific binding activity, and specific examples include $F(ab')_2$, Fab', Fab, Fv, sFv, dsFv, sdAb and the like (Exp. Opin. Ther. Patents, Vol. 6, No. 5, p. 441-456, 1996). The class of antibody is not particularly limited, and encompasses an antibody having any isotype of IgG, IgM, IgA, IgD or IgE and the like. Preferred is IgG or IgM, and more preferred is IgG in consideration of easiness of the purification and the like.

Using the antibody of the present invention, the bacterium of the present invention can be detected, quantified and the like by an immunological method. Examples of the immunological method include, but are not limited to, flow cytometry analysis, radioisotope immunity measurement method (RIA method), ELISA method (Methods in Enzymol. 70: 419-439 (1980)), western blotting, immunohistological staining and the like.

The contents disclosed in any publication cited in the present specification, including patents and patent applications, are hereby incorporated in their entireties by reference, to the extent that they have been disclosed herein.

While the present invention is explained in more detail in the following by referring to Examples, the present invention is not limited in any way by the Examples shown below.

EXAMPLES

[Example 1] Blood Glucose Level and Analysis of Enteric Bacterial Flora of Obesity Model Mouse Since B6.V-Lep$^{ob}$/J(ob/ob) mouse is a mouse deficient in leptin, which is one kind of appetite-suppressing hormone, it shows obesity due to overeating. However, an individual showing a high fasting blood glucose level exceeding 400 mg/dl is rare.

Thus, to examine the relationship between blood glucose level and enteric bacterial flora of obesity model mouse, 6 male ob/ob mice (5-week-old) were purchased from Charles River Laboratories Japan, Inc., and bred for 6 weeks, during which the fasting blood glucose level (16 hr fasting) and enteric bacterial flora in the feces at the time point of the start of breeding (5-week-old) were measured. During the breeding period, the mice were bred at one mouse/cage under light-dark 12 hr cycle SPF conditions with free access to water and CRF-1 (manufactured by Oriental Yeast Co., Ltd.). The blood glucose level was measured by FUJI DRI-CHEM system FDC7000V. The excreted feces was directly received in a container containing 99% ethanol, and preserved at −30° C. until use. For DNA extraction from the feces, FastDNA SPIN Kit for Soil (manufactured by MP biomedicals) was used. The enteric bacterial flora in the feces was measured by Terminal Restriction Fragment Length Polymorphism (T-RFLP) method (Micorbiol. Immunol., 47:133-142, 2003) and using Genetic Analyzer 3130xl and DNA Size Standard 1200LIZ (Applied Biosystems). The PCR product of 16S rRNA gene was digested with MspI (manufactured by Takara).

Figure 2:
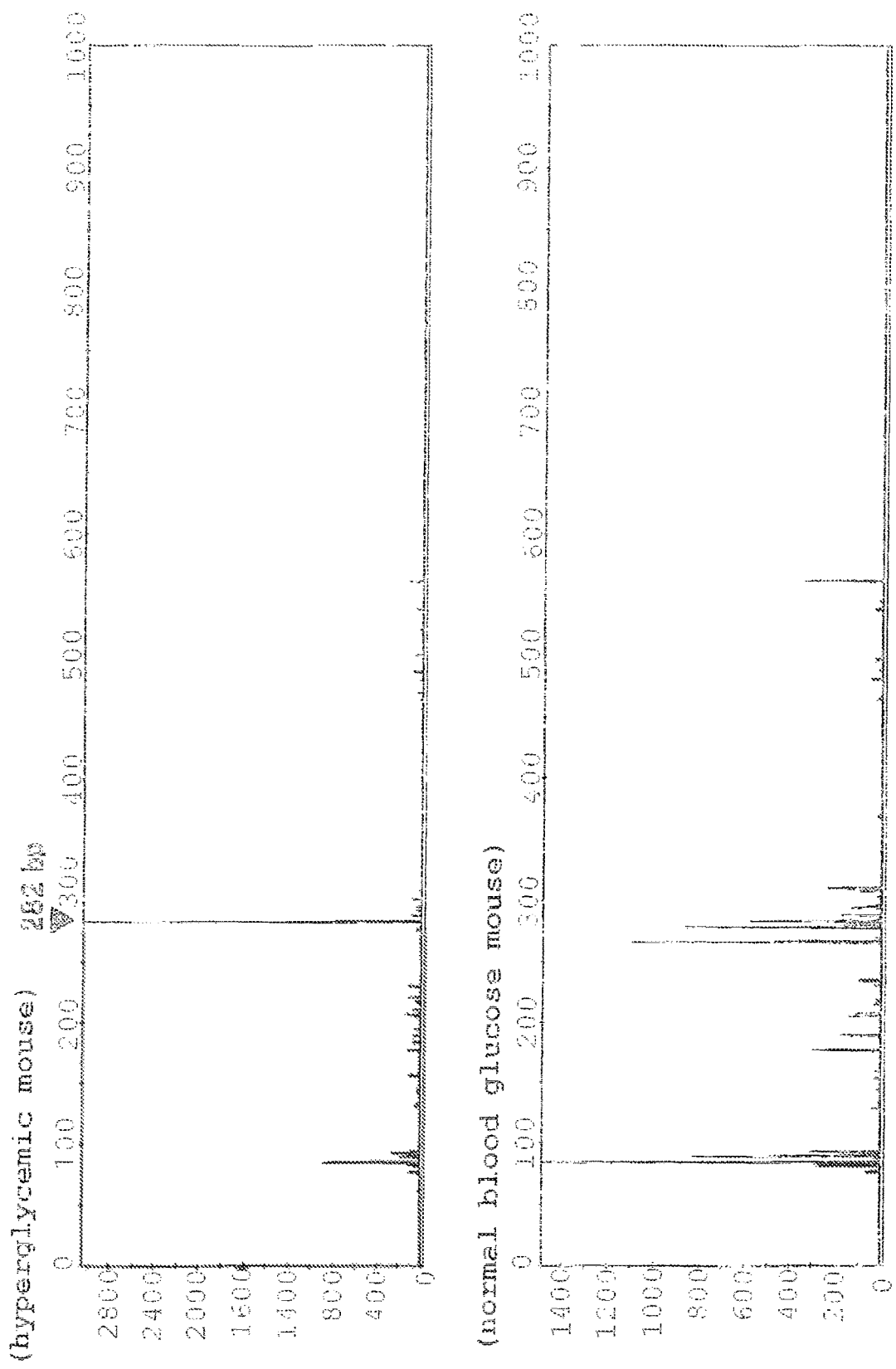
FIG. 2 shows the enteric bacterial flora at the time of the start of breeding (5-week-old). The enteric bacterial flora of mice that showed an increase in the fasting blood glucose level (upper). The enteric bacterial flora of mice that showed a normal blood glucose level (below).

As shown in FIG. 1, in one out of 6 mice bred, fasting blood glucose level increased, and exceeded 400 mg/dl at 6 weeks (time point of 11-week-old) from the start of breeding. The enteric bacterial flora of this animal was examined to find that, as shown in FIG. 2, a particular enteric bacterium having a length of restriction enzyme-treated fragment (T-RF) of 282±1 bp became dominant at the time point of the start of breeding (5-week-old).

[Example 2] Suppressive Effect of Antibiotic Treatment of Diabetes Model Mouse on Fasting Blood Glucose Level Increase Since BKS.Cg-m+/+Lepr$^{db}$/J(db/db) mouse is a leptin receptor deficient mouse, which is one kind of appetite-suppressing hormone, it shows obesity due to overeating like ob/ob mouse. Thereafter, almost all db/db mice develop diabetes showing a fasting blood glucose level exceeding 400 mg/dl.

To examine the influence of poorly absorbed antibiotic on the fasting blood glucose level of the diabetes model mouse, 12 male db/db mice (5-week-old) were purchased from Charles River Laboratories Japan, Inc., divided into a control group (water ingestion, 6 mice) and vancomycin administration group (1 mg/ml vancomycin in drinking water, 6 mice), bred for 8 weeks by a method similar to that in Example 1, and the fasting blood glucose level and enteric bacterial flora in the feces were measured. Vancomycin is a glycopeptide antibacterial agent, which is an antibiotic characterized in that it shows a broad antibacterial spectrum against Gram-positive bacteria, it is not easily decomposed in the gastrointestinal tract, is scarcely absorbed into the body and, when orally ingested, it acts only on enteric bacteria.

Figure 3:
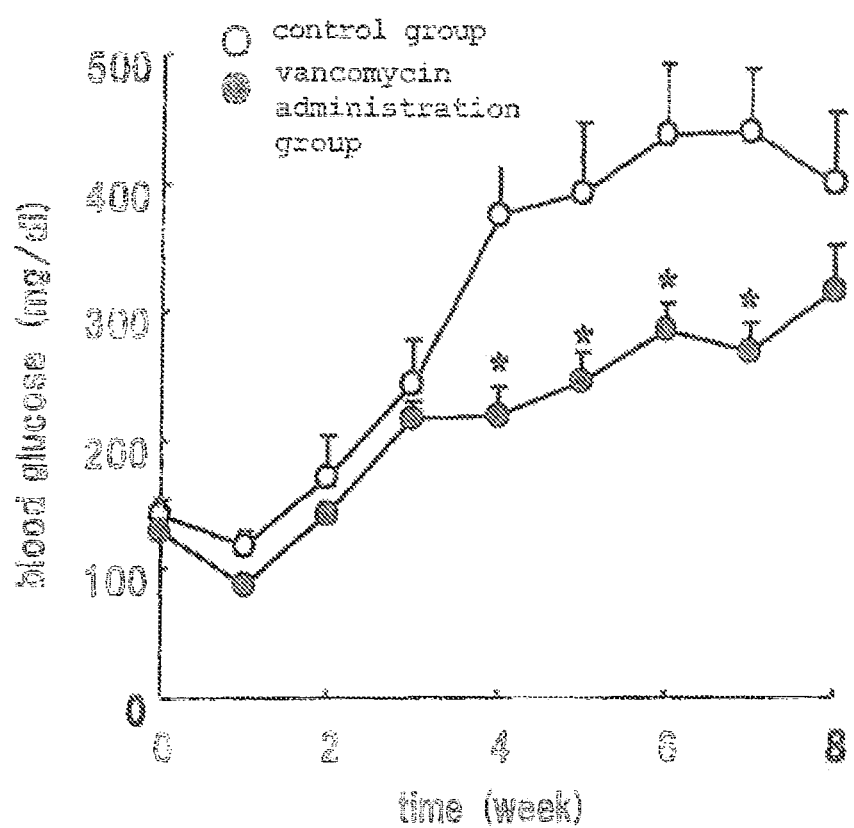
FIG. 3 shows a suppressive effect of vancomycin on an increase in the fasting blood glucose level. The data shows mean±standard error (n=6, *: P<0.05 (comparison with control group)).
Figure 4:
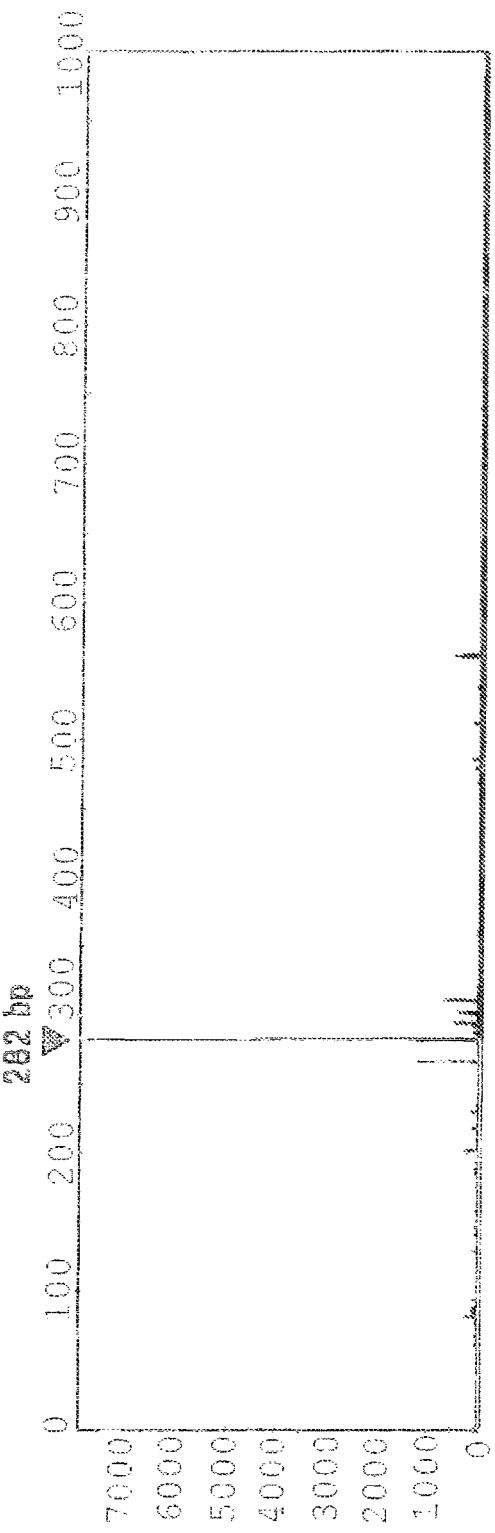
FIG. 4 shows changes in the enteric bacterial flora due to the ingestion of vancomycin by an individual that showed the highest level of T-RF 282±1 bp.
Figure 4:
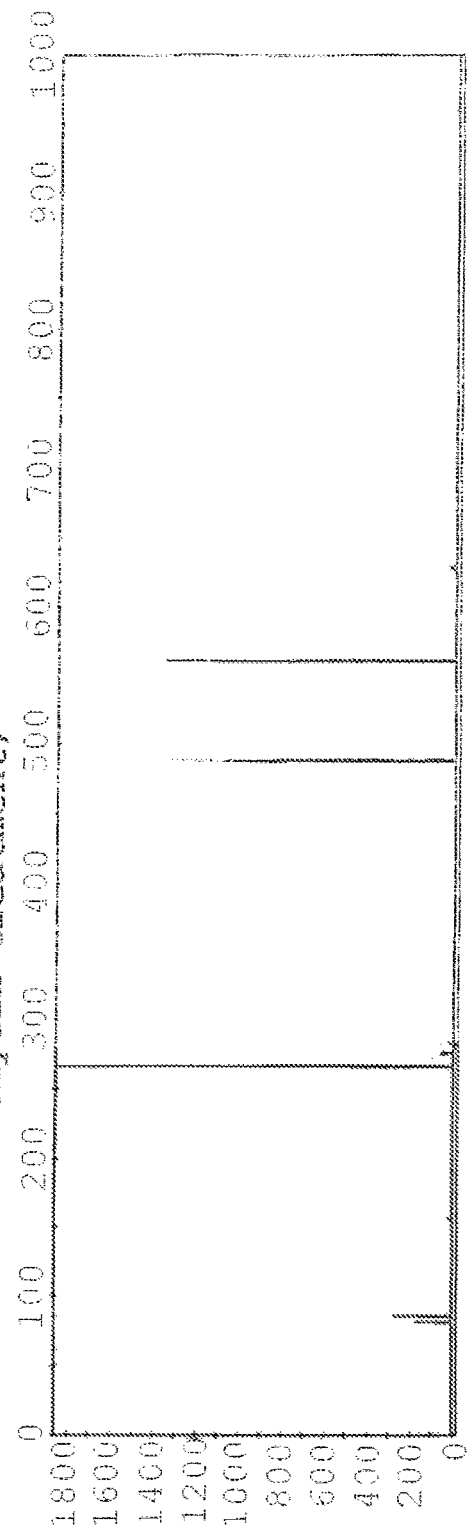

As shown in FIG. 3, the fasting blood glucose level of the vancomycin administration group was significantly lower than that of the control group, and it was clarified that an increase in the fasting blood glucose level is suppressed by a poorly absorbed antibiotic. Moreover, as a result of vancomycin administration, an enteric bacterium having T-RF 282±1 bp was below detection limit.

[Example 3] Isolation and Identification of Enteric Bacterium with T-RF 282±1 bp Ten 5-week-old male db/db mice were purchased from Charles River Laboratories Japan, enteric bacterial flora in the feces was measured by the T-RFLP method, and one mouse showing a particularly high amount of T-RF 282±1 bp was selected. The cecum contents (about 50 mg) of the selected mouse was taken, suspended in 1 ml of 99% ethanol and treated m for 2 hr, diluted with anaerobic PBS, applied to EG agar medium (Lab Anim 19: 111-118, 1985), and anaerobically cultured at 37° C. for 7 days. Emerged 60 colonies were isolated, each colony was subjected to a measurement by the T-RFLP method, and colony having T-RF 282±1 bp was identified and established.

The nucleotide sequence of the 16S ribosomal RNA gene (16S rDNA) of this strain is shown by SEQ ID NO: 3.

Figure 5:
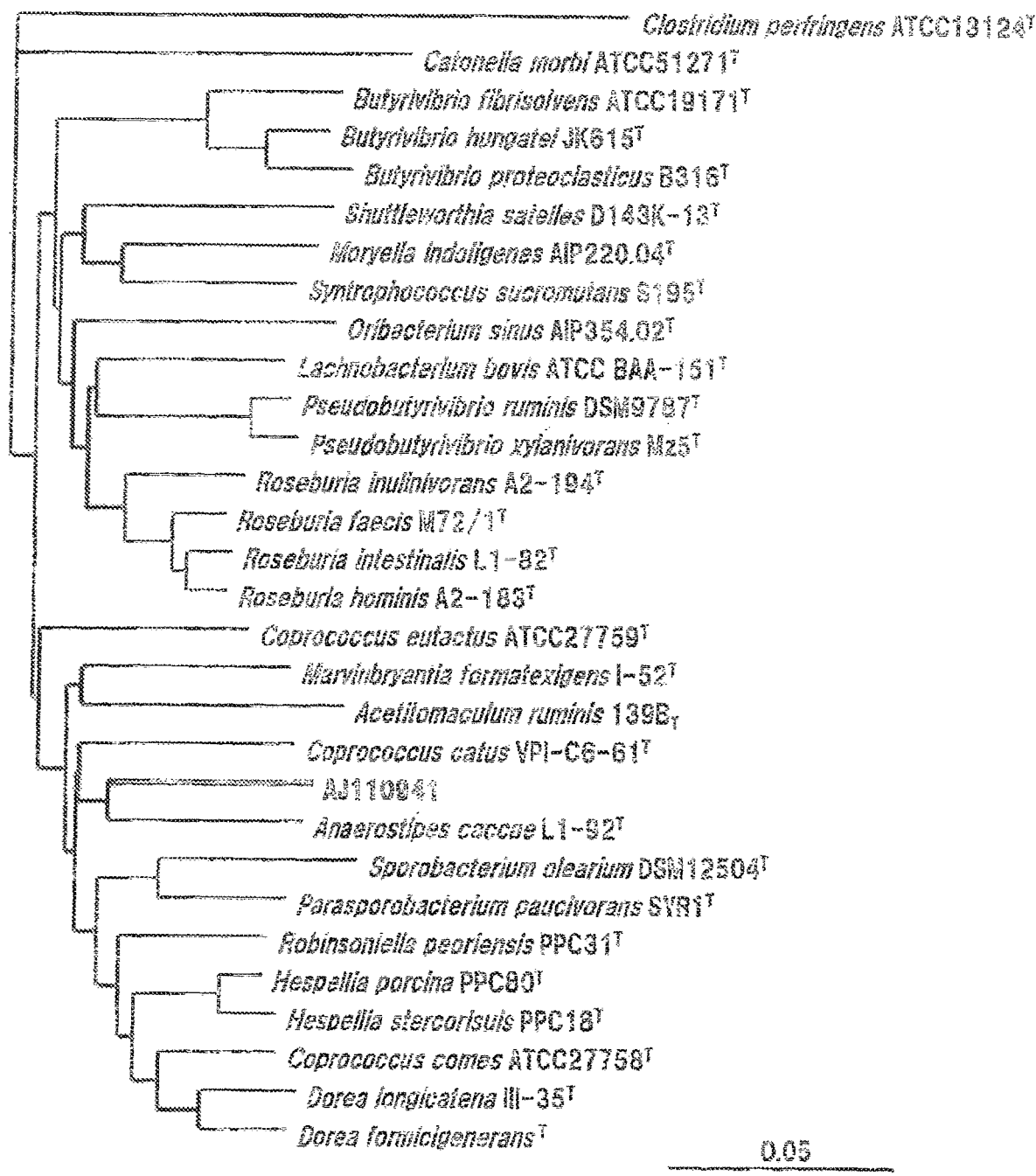
FIG. 5 shows the molecular phylogenetic tree analysis results of a Neighbor Joining method using 16S rDNA of the isolated strain.

Based on this sequence, a lineage classification analysis of the bacterium species was performed by reference to the databases of Japan DNA data bank (http://www.ddbj.nig.ac.jp) and Ribosomal Database Project (http://rdp.cme.msu.edu/). As a result, it was clarified to be a bacterium belonging to Firmicutes Clostridia Clostridiales Lachnospiraceae (FIG. 5). However, even the closest-related Anaerostipes caccae L1-92$^T$ strain showed a homology of 90% to the 16S rDNA sequence (Table 1). NCBI BLAST was used for the calculation of the homology.

TABLE 1

| Accession No. | Type Strain | homology |
|---|---|---|
| AJ270487 | Anaerostipes caccae L1-92$^T$ | 90% |
| AJ505973 | Marvinbryantia formatexigens I-52$^T$ | 90% |
| AF445239 | Hespellia porcina PPC80$^T$ | 89% |
| AF445264 | Hespellia stercorisuis PPC18$^T$ | 89% |
| AF445285 | Robinsoniella peoriensis PPC31$^T$ | 89% |
| AJ132842 | Dorea longicatena III-35$^T$ | 89% |
| DQ377947 | Moryella indoligenes AIP220.04$^T$ | 89% |
| EF031542 | Coprococcus comes ATCC27758$^T$ | 89% |

TABLE 1-continued

| Accession No. | Type Strain | homology |
|---|---|---|
| AB038359 | Coprococcus catus VPI-C6-61$^T$ | 88% |
| AF298663 | Lachnobacterium bovis ATCC BAA-151$^T$ | 88% |
| AJ270473 | Roseburia inulinivorans A2-194$^T$ | 88% |
| AJ270482 | Roseburia hominis A2-183$^T$ | 88% |
| AJ272036 | Parasporobacterium paucivorans SYR1$^T$ | 88% |
| AJ312385 | Roseburia intestinalis L1-82$^T$ | 88% |
| AY305310 | Roseburia faecis M72/1$^T$ | 88% |
| AY323228 | Oribacterium sinus AIP354.02$^T$ | 88% |
| EF031543 | Coprococcus eutactus ATCC27759$^T$ | 88% |
| X95893 | Pseudobutyrivibrio ruminis DSM9787$^T$ | 88% |
| AF116854 | Sporobacterium olearium DSM12504$^T$ | 87% |
| AF202264 | Syntrophococcus sucromutans S195$^T$ | 87% |
| AF399956 | Shuttleworthia satelles D143K-13$^T$ | 87% |
| AJ428548 | Pseudobutyrivibrio xylanivorans Mz5$^T$ | 87% |
| AJ428553 | Butyrivibrio hungatei JK615$^T$ | 87% |
| L34619 | Dorea formicigenerans$^T$ | 87% |
| U37378 | Butyrivibrio proteoclasticus B316$^T$ | 87% |
| U41172 | Butyrivibrio fibrisolvens ATCC19171$^T$ | 87% |
| M59083 | Acetitomaculum ruminis 139B$^T$ | 86% |
| X87151 | Catonella morbi ATCC51271$^T$ | 86% |
| CP000246 | Clostridium perfringens ATCC13124$^T$ | 84% |

Figure 6:
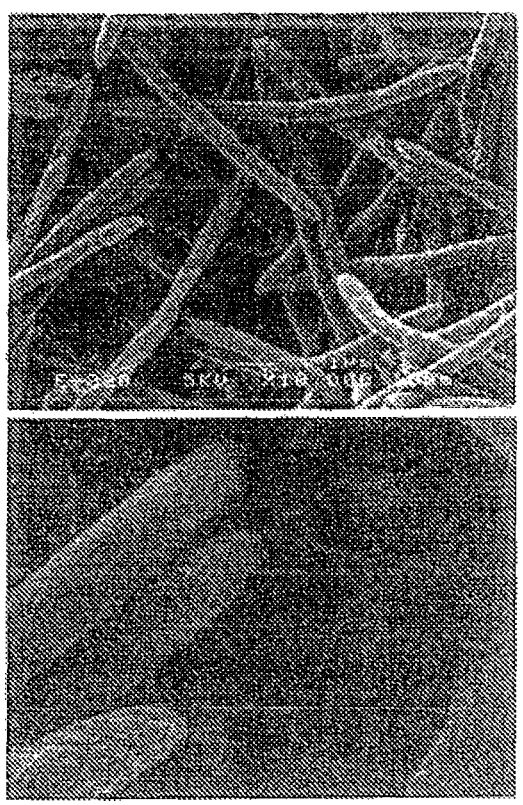
FIG. 6 shows a scanning electron microscopic image of AJ110941 strain.

It is generally known that identification at a genus level requires homology of not less than 95%, and identification at a species level requires homology of not less than 98% (Science 2005, 307, 1915-1920). Therefore, AJ110941 was clarified to be a new species of a new genus without a scientific name. As a result of scanning electron microscopic observation of the culture strain, it was found to be, as shown in FIG. 6, bacterium bacillus having a length of about 10 μm, width of about 1 μm and many pili or flagella around the cell (hereinafter this enteric bacterium is referred to as AJ110941).

[Example 4] AJ110941 Motility Confirmation Test

AJ110941 bacteria were scraped for one loop amount with a 1 μl loop, smeared on the center of an EG agar medium in a uniform disc shape with diameter about 1 cm, and cultured under anaerobic conditions at 37° C. for 7 days. As a result, the growth range of the bacteria began to expand in a disc shape from the third day after the start of the culture, and the growth range expanded to about 5 cm on day 5, and about 9 cm on day 7. In this way, remarkable expansion of the growth range was observed. AJ110941 bacteria was inoculated by puncture to a semisolid stab EG medium prepared to an agar concentration of 0.15%, and anaerobically cultured at 37° C. for 7 days. As a result, the whole semisolid stab EG medium became cloudy. Therefrom it was judged that AJ110941 has motility.

[Example 5] Production of Specific DNA Primers for AJ110941 Detection

Based on the 16S rDNA sequence shown in Example 3, specific DNA primers for AJ110941 detection were designed. 161-183F: 5'-CGCACAGCTTCGCATGAAGTGGT-3' (SEQ ID NO: 1) 438-458R: 5'-ACCGTCTGGCGACCCAAAGGT-3' (SEQ ID NO: 2)

To evaluate specificity of the primer set, PCR was performed with a template of DNAs derived from various representative enteric bacteria. For PCR, 30 cycles of 94° C. 30 seconds, 60° C. 30 seconds, 72° C. 30 seconds were performed using Ex taq (TAKARA BIO INC), and PCR product was detected. As a result, as shown in Table 2, about 300 bp PCR was detected only in AJ110941. This enabled confirmation of the specificity of the designed primers.

TABLE 2

| strain | PCR results (+/−) |
|---|---|
| AJ110941 | + |
| *Bacteroides distasonis* JCM5825 | − |
| *Bacteroides fragilis* JCM11019 | − |
| *Bacteroides thetaiotaomicron* JCM5827 | − |
| *Bacteroides vulgatus* JCM5826 | − |
| *Bifidobacterium adolescentis* JCM1275 | − |
| *Bifidobacterium adolescentis* JCM7042 | − |
| *Bifidobacterium bifidum* JCM1254 | − |
| *Bifidobacterium bifidum* JCM1255 | − |
| *Bifidobacterium breve* JCM1192 | − |
| *Bifidobacterium breve* JCM7017 | − |
| *Bifidobacterium catenulatum* JCM1194 | − |
| *Bifidobacterium dentium* JCM1195 | − |
| *Bifidobacterium dentium* JCM7135 | − |
| *Bifidobacterium infantis* JCM1222 | − |
| *Bifidobacterium longum* JCM1217 | − |
| *Bifidobacterium pseudocatenulatum* JCM1200 | − |
| *Bifidobacterium pseudocatenulatum* JCM7040 | − |
| *Blautia producta* JCM1471 | − |
| *Clostridium bifermentans* JCM1386 | − |
| *Clostridium butyricum* JCM1391 | − |
| *Clostridium paraputrificum* JCM1293 | − |
| *Clostridium perfringens* JCM1290 | − |
| *Clostridium ramosum* JCM1298 | − |
| *Collinsella aerofaciens* JCM10188 | − |
| *Collinsella intestinalis* JCM10643 | − |
| *Collinsella stercoris* JCM10641 | − |
| *Eggerthella lenta* JCM9979 | − |
| *Enterococcus faecalis* JCM5803 | − |
| *Enterococcus faecium* JCM5804 | − |
| *Escherichia coli* JCM1649 | − |
| *Eubacterium limosum* JCM6421 | − |
| *Faecalibacterium prausnitzii* ATCC27766 | − |
| *Fusobacterium varium* JCM3722 | − |
| *Lactobacillus acidophilus* JCM1132 | − |
| *Lactobacillus acidophilus* JCM1229 | − |
| *Lactobacillus casei* JCM1134 | − |
| *Lactobacillus gasseri* JCM1131 | − |
| *Lactobacillus salivalius* JCM1231 | − |
| *Mitsuokella multiacida* JCM2054 | − |
| *Porphyromonas gingivaris* JCM12257 | − |
| *Prevotella melaninogenica* JCM6325 | − |

[Example 6] Analysis of AJ110941-Colonized Gnotobiotic ob/ob Mouse Phenotype

To verify involvement of enteric bacterium AJ110941 isolated in Example 3 in an increase in the blood glucose level of obesity model mouse, the bacteria were colonized in germ-free obesity model mouse free of an influence of other enteric bacteria, and an influence on the blood glucose level was examined.

5-week-old male C57BL/6JHamSlc-ob/ob germ-free mice were purchased from Sankyo Labo Service Corporation, and acclimated under germ-free conditions until they became 8 weeks of age. Thereafter, they were grouped into a control (germ-free) group (n=3), an *E. coli* colonization group (n=3), and an *E. coli* and AJ110941 co-colonization group (n=3). Cultivated bacteria of *E. coli* and AJ110941 were each inoculated orally to establish gnotobiotic mice, and the mice were further bred for 6 weeks. After 6 weeks, they were fasted for 4 hr, and enteric bacterial flora in the feces, blood glucose level, insulin, and glucagon were measured. The enteric bacterial flora and blood glucose level were measured in the same manner as in Example 1. Insulin ELISA kit (manufactured by Morinaga Institute of Biological Science, Inc.) was used for the insulin measurement, and glucagon ELISA kit wako (manufactured by Wako Pure Chemical Industries, Ltd.) was used for the glucagon measurement.

Since growth of AJ110941 requires high anaerobicity, co-colonization with facultative anaerobic *E. coli* enabled colonization of AJ110941 in a germ-free mouse. Throughout the entire period of from the purchase of the mice to the completion of breeding thereof, the mice were bred in an isolator capable of maintaining germ-free conditions at 3 mice/cage, and allowed to freely take water and CRF-1 (manufactured by Oriental Yeast Co., Ltd.).

Figure 7:
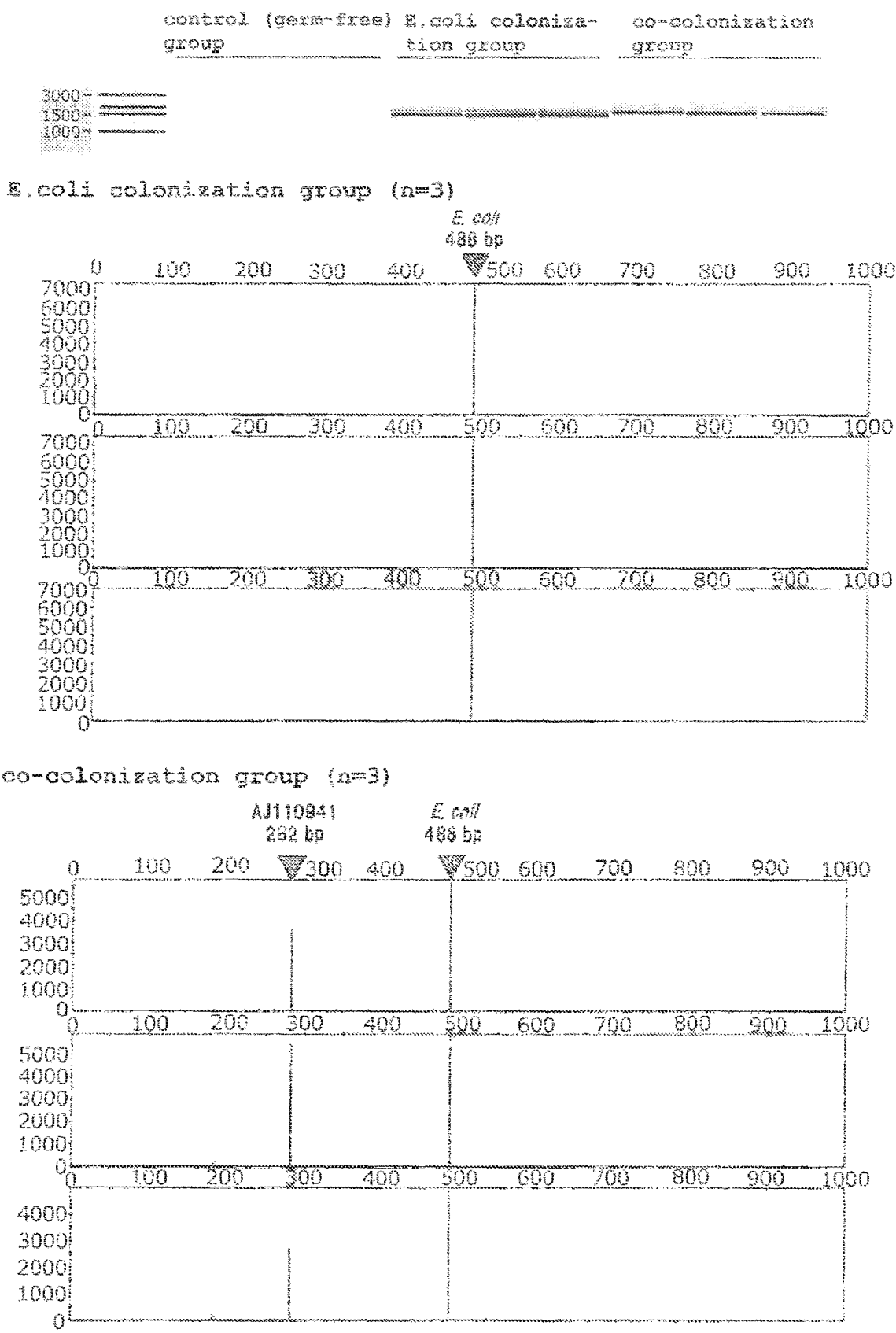
FIG. 7 shows the measurement results of enteric bacterial flora of gnotobiotic mice.
Figure 8:
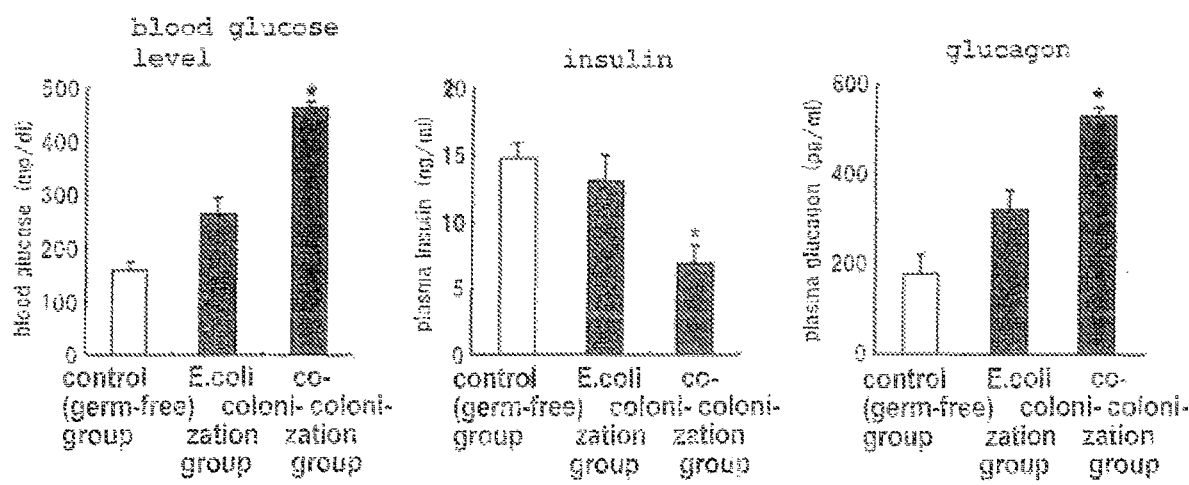
FIG. 8 shows an influence of AJ110941 strain colonization on the blood glucose level, blood insulin and glucagon (n=3, *: P<0.05 (comparison with control group)).
Figure 9:
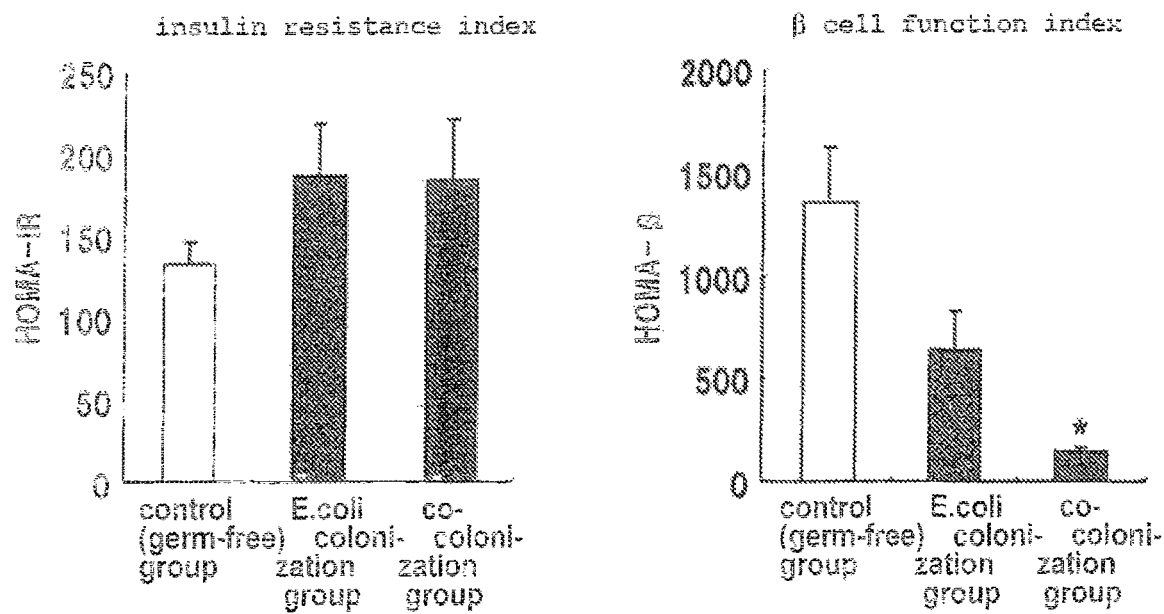
FIG. 9 shows an influence of AJ110941 strain colonization on HOMA-IR and HOMA-β (n=3, *: P<0.05 (comparison with control group)).

First, enteric bacterial flora in the feces was measured at the completion of breeding and colonization of the inoculated bacterium was confirmed. In the control group, the germ-free state was maintained, *E. coli* alone was detected in the *E. coli* colonization group and only *E. coli* and AJ110941 were detected in the co-colonization group (FIG. 7), whereby generation of the object gnotobiotic mouse was confirmed. The blood components were measured to find a remarkable increase in the blood glucose level, an increase in the blood glucagon concentration, and a decrease in the blood insulin concentration in the co-colonization group (FIG. 8). Furthermore, insulin resistance index (HOMA-IR) and pancreatic β cell function index (HOMA-β) were determined from the results of the blood glucose level and insulin. As a result, no intergroup difference was found in HOMA-IR but a remarkable decrease in HOMA-β was shown in the co-colonization group (FIG. 9).

Therefore, it was clarified that colonization of AJ110941 under conditions eliminating an influence of other enteric bacteria as much as possible causes decreased function of pancreatic β cells, namely, lowering of insulin secretion capability, which in turn causes hyperglycemia.

[Example 7] Influence on Insulin Resistance by Oral Administration of AJ110941 Live Bacteria to Diet-Induced Obesity Model Mouse C57BL/6J (Charles River Laboratories Japan) induced to be obese by taking a 60 kcal % lard high-fat diet (manufactured by Research Diet) from 4-week-old to 12-week-old were divided into 3 groups (control group, *E. coli* administration group, AJ110941 administration group). Each group was loaded with *E. coli* and AJ110941 bacteria prepared when in use at a dose of about $10^6$ cells/350 μl/mouse once per day for 4 weeks by oral administration. The mice were bred under SPF conditions at 1 mouse/cage with free access to water and 60 kcal % lard high-fat diet. AJ110941 bacteria was anaerobically cultured (oxygen concentration not more than 1 ppm) in an EG agar medium and, in an anaerobic chamber, colonies were collected by a loop, suspended in an EG liquid medium, sealed in a syringe for oral administration at a bacteria dose of about $10^6$ cells/350 μl per mouse, and maintained in a tightly closed container until immediately before administration to keep the anaerobic state. *E. coli* was subjected to aerobic culture in an EG agar medium, suspended in an EG liquid medium, and orally administered at a bacteria dose of about $10^6$ cells/350 μl per mouse. The control group was administered with only the EG liquid medium used for suspending the bacteria. Four weeks from the start of the bacteria administration, an insulin tolerance test (insulin 1 U/kg, i.p.) was performed, and an influence of AJ110941 on the insulin resistance was examined.

Figure 10:
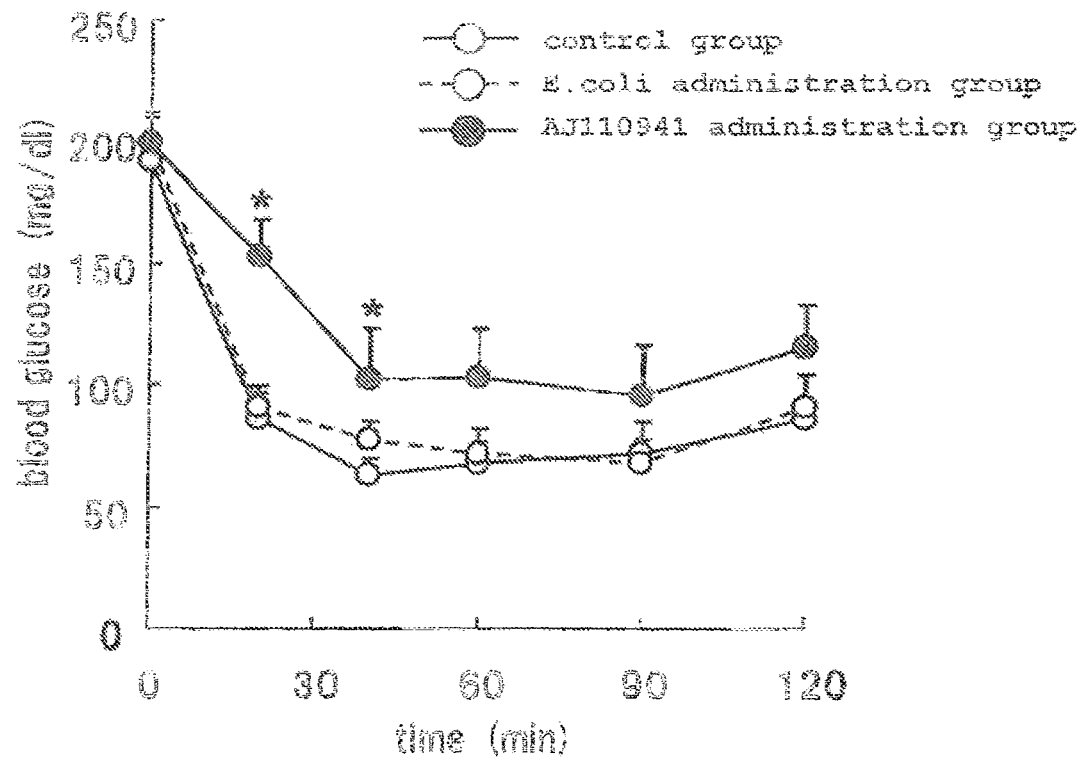
FIG. 10 shows an influence of oral loading of AJ110941 strain on the insulin sensitivity (n=5, *: P<0.05 (comparison with control group)).

As a result, the blood glucose level rapidly decreased after insulin administration in the control group and the *E. coli* administration group, and the decrease was significantly suppressed in the AJ110941 administration group (FIG. 10).

Therefore, it was clarified that oral loading of AJ110941 live cells under SPF conditions decreases insulin sensitivity and induces insulin resistance.

[Example 8] Analysis of Relationship Between the Presence of AJ110941 and Diabetes in Human Feces was collected from healthy test subjects (31 subjects) (BMI≤23, fasting blood glucose<100 mg/dl, HbA1c<5.8%), obesity test subjects (32 subjects) (BMI≥25, fasting blood glucose<100 mg/dl, HbA1c<5.8%), and type 2 diabetes test subjects (31 subjects) (BMI≥25, fasting blood glucose≥126 mg/dl, HbA1c≥6.1%), and the relationship between the presence of AJ110941 in human and diabetes index was examined with the primer set described in Example 4.

Figure 11:
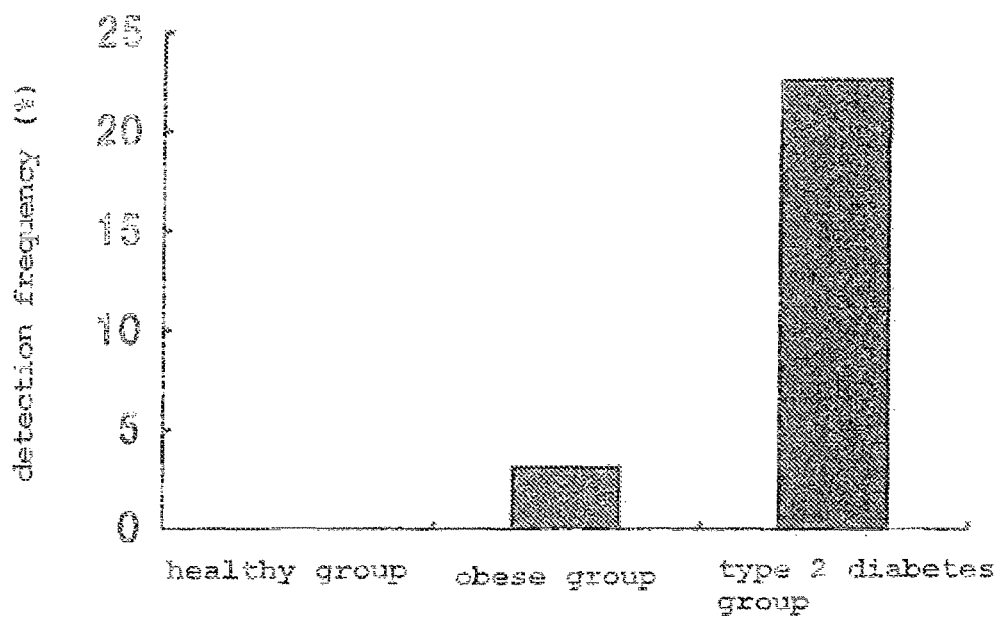
FIG. 11 shows the detection frequency of AJ110941 in human.
Figure 12:
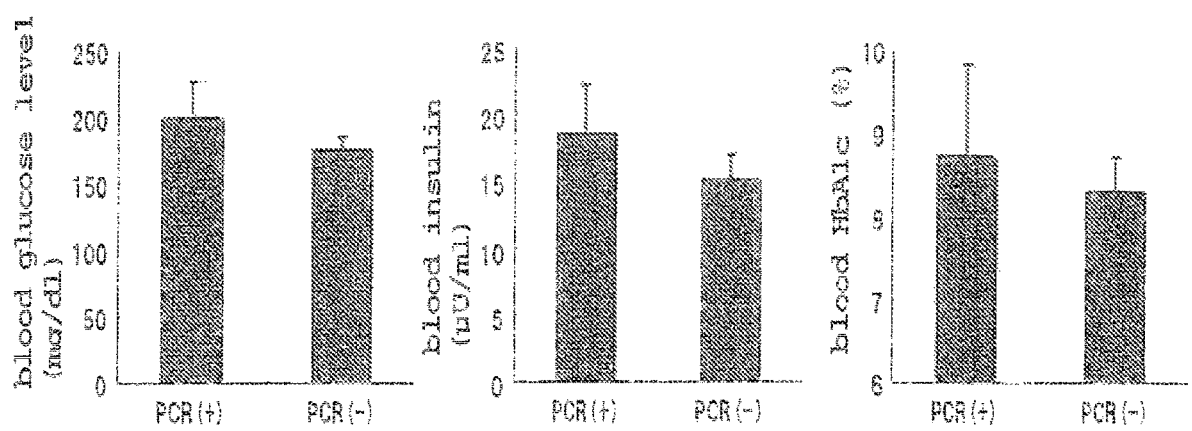
FIG. 12 shows the comparison of the diabetes index between AJ110941 carriers and non-carriers in type 2 diabetes test subjects.

The feces sample of the test subject was suspended in GTC solution (4M guanidium thiocyanate, 40 mM EDTA, 100 mM Tris-HCl (pH 9.0)), and DNA was extracted and purified using Fast DNA SPIN kit for soil (manufactured by MP-biomedicals) and subjected to PCR. The PCR conditions were the same as those in Example 4. As a result, the number of detection case in PCR with the AJ110941 specific primers was 0 for the healthy test subject group, 1 (3.1%) for the obesity test subject group, and 7 (22.5%) for the type 2 diabetes test subject group, and the detection frequency was the highest in the type 2 diabetes test subject group (FIG. 11). In addition, the type 2 diabetes test subject group was divided into a PCR positive (+) test subject group (7 subjects) and a PCR negative (−) test subject (24 subjects), and compared for the fasting blood glucose level, blood insulin and blood HbA1c, which are diabetes indices. As a result, the PCR(+) group showed high tendency in all indices (FIG. 12). Therefore, this shows the possibility that AJ110941 bacterium is also present in human, and acts as an aggravation factor of diabetes.

INDUSTRIAL APPLICABILITY

The bacterium of the present invention that induces the onset of diabetes can be a new medicament target in the field of prophylaxis or treatment of diabetes. This enables research and development of pharmaceutical products such as antibiotic, vaccine and the like aiming at the prophylaxis or treatment of diabetes, and research and development of foods such as prebiotics, probiotics and the like. Furthermore, the risk of the onset of diabetes can be confirmed by testing an enteric bacterium in the feces.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A bacterium isolated from intestinal flora, which exhibits a diabetes inducing activity, and which belongs to Lachnospiraceae,
wherein said bacterium has a 16S ribosomal RNA gene comprising a nucleic acid sequence having a homology of not less than 98% to the nucleic acid sequence shown by SEQ ID NO: 3,
wherein the bacterium is identified by the accession number FERM BP-11443, and
wherein said bacterium is in an anaerobic culture in EG liquid medium or EG agar medium, and has lost resistance to an organic solvent by said culture.

2. A bacterium according to claim 1, which is a *bacillus*.

3. A bacterium according to claim 1, which has a pilus or flagellum-like structure.

4. A bacterium according to claim 1, which exhibits motility.

5. A bacterium according to claim 1, which is anaerobic.

6. A bacterium according to claim 1, wherein the organic solvent to which the bacterium has lost resistance is ethanol.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: synthetic primer

<400> SEQUENCE: 1
cgcacagctt cgcatgaagt ggt                                          23

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
accgtctggc gacccaaagg t                                            21

<210> SEQ ID NO 3
<211> LENGTH: 1469
<212> TYPE: DNA
<213> ORGANISM: Unknown
<220> FEATURE:
<223> OTHER INFORMATION: 16S ribosomal RNA gene

<400> SEQUENCE: 3
```

```
aggatgaacg ctggcggcgt gcttaacaca tgcaagtcga acgggcctca tattgaaacc    60
tagtgattta tgagttagtg gcggacgggt gagtaacgcg tggaaaacct gccgtatact   120
gggggataac acttagaaat aggtgctaat accgcataag cgcacagctt cgcatgaagt   180
ggtgtgaaaa actctggtgg tatacgatgg ttccgcgtct gattagcttg ttggcggggt   240
aatggctcac caaggcgacg atcagtagcc ggcctgagag ggtgaacggc cacattggga   300
ctgagacacg gcccaaactc ctacgggagg cagcagtggg gaatattgca caatggggga   360
aaccctgatg cagcgacgcc gcgtgagtga agaagtattt cggtatgtaa agctctatca   420
gcagggaaga aatagcgacc tttgggtcgc cagacggtac ctgattaaga agccccggct   480
aactacgtgc cagcagccgc ggtaatacgt aggggggcaag cgttatccgg atttactggg   540
tgtaaaggga gcgtagacgg cagcacaagt ctgaagtgaa atgccggggc ttaaccccgg   600
aactgctttg gaaactgtgc agctagagtg caggagaggt aagtggaatt cctagtgtag   660
cggtgaaatg cgtagatatt aggaggaaca ccagtggcga aggcggctta ctggactgta   720
actgacgttg aggctcgaaa gcgtggggag caaacaggat tagataccct ggtagtccac   780
gctgtaaacg atgattacta ggtgttgggg accaaggtc cttcggtgcc gtcgcaaacg   840
cattaagtaa tccacctggg gagtacgttc gcaagaatga aactcaaagg aattgacggg   900
gacccgcaca gcggtggag catgtggttt aattcgaagc aacgcgaaga accttacctg   960
gtcttgacat cccgatgacg agtgagcaaa gtcactttcc cttcggggca ttggagacag  1020
gtggtgcatg gttgtcgtca gctcgtgtcg tgagatgttg ggttaagtcc gcaacgagc   1080 gcaacccta tttccagtag ccagcaagaa agatgggaac tctggagaga ctgcccggga  1140
taactgggag gaaggcgggg atgacgtcaa atcatcatgc cccttatgat cagggctaca  1200
cacgtgctac aatggcgtaa acaaagggaa gcgaagtggt gacacgaagc aaatccgaaa  1260
aacaacgtct cagttcggat tgtagtctgc aactcgacta catgaagctg gaatcgctag  1320
taatcgcgaa tcagaatgtc gcggtgaata cgttcccggg tcttgtacac accgcccgtc  1380
acaccatggg agtcggaaat gcccgaagtc agtgacccaa ccgagaggag ggagctgccg  1440
aaggtggagc cggtaactgg ggtgaagtc                                   1469
```

```
<210> SEQ ID NO 4
<211> LENGTH: 42
<212> TYPE: DNA
<213> ORGANISM: Unknown
<220> FEATURE:
<223> OTHER INFORMATION: partial sequence of SEQ ID No: 3

<400> SEQUENCE: 4
aacgggcctc atattgaaac ctagtgattt atgagttagt gg                        42

<210> SEQ ID NO 5
<211> LENGTH: 69
<212> TYPE: DNA
<213> ORGANISM: Unknown
<220> FEATURE:
<223> OTHER INFORMATION: partial sequence of SEQ ID No: 3

<400> SEQUENCE: 5
cgcataagcg cacagcttcg catgaagtgg tgtgaaaaac tctggtggta tacgatggtt    60
ccgcgtctg                                                            69

<210> SEQ ID NO 6
<211> LENGTH: 64
```

```
<212> TYPE: DNA
<213> ORGANISM: Unknown
<220> FEATURE:
<223> OTHER INFORMATION: partial sequence of SEQ ID No: 3

<400> SEQUENCE: 6
gctctatcag cagggaagaa atagcgacct ttgggtcgcc agacggtacc tgattaagaa      60
gccc                                                                  64

<210> SEQ ID NO 7
<211> LENGTH: 53
<212> TYPE: DNA
<213> ORGANISM: Unknown
<220> FEATURE:
<223> OTHER INFORMATION: partial sequence of SEQ ID No: 3

<400> SEQUENCE: 7
cagcacaagt ctgaagtgaa atgccggggc ttaaccccgg aactgctttg gaa             53

<210> SEQ ID NO 8
<211> LENGTH: 43
<212> TYPE: DNA
<213> ORGANISM: Unknown
<220> FEATURE:
<223> OTHER INFORMATION: partial sequence of SEQ ID No: 3

<400> SEQUENCE: 8
attactaggt gttgggggac caaggtcctt cggtgccgtc gca                        43

<210> SEQ ID NO 9
<211> LENGTH: 48
<212> TYPE: DNA
<213> ORGANISM: Unknown
<220> FEATURE:
<223> OTHER INFORMATION: partial sequence of SEQ ID No: 3

<400> SEQUENCE: 9
cccgatgacg agtgagcaaa gtcactttcc cttcggggca ttggagac                   48

<210> SEQ ID NO 10
<211> LENGTH: 60
<212> TYPE: DNA
<213> ORGANISM: Unknown
<220> FEATURE:
<223> OTHER INFORMATION: partial sequence of SEQ ID No: 3

<400> SEQUENCE: 10
ctatttccag tagccagcaa gaaagatggg aactctggag agactgcccg ggataactgg      60

<210> SEQ ID NO 11
<211> LENGTH: 57
<212> TYPE: DNA
<213> ORGANISM: Unknown
<220> FEATURE:
<223> OTHER INFORMATION: partial sequence of SEQ ID No: 3

<400> SEQUENCE: 11
gcgtaaacaa agggaagcga agtggtgaca cgaagcaaat ccgaaaaaca acgtctc         57

<210> SEQ ID NO 12
<211> LENGTH: 50
<212> TYPE: DNA
<213> ORGANISM: Unknown
<220> FEATURE:
<223> OTHER INFORMATION: partial sequence of SEQ ID No: 3
```

```
<400> SEQUENCE: 12
tcggaaatgc ccgaagtcag tgacccaacc gagaggaggg agctgccgaa        50

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
agagtttgat cctggctcag                                         20

<210> SEQ ID NO 14
<211> LENGTH: 19
<212> TYPE: DNA
<213> ORGANISM: Artificial Sequence
<220> FEATURE:
<223> OTHER INFORMATION: synthetic primer

<400> SEQUENCE: 14
ggttaccttg ttacgactt                                          19
```